United States Patent [19]

Chambon et al.

[11] Patent Number: 5,861,381
[45] Date of Patent: Jan. 19, 1999

[54] PHARMACEUTICAL COMPOSITION FOR THE TREATMENT OF A MALIGNANT TUMOR

[75] Inventors: Pierre Chambon, Blaesheim; Marie-Paule Kieny, Strasbourg, both of France; Richard Lathe, Leeds, Great Britain; Mara Hareuveni, Ramat-Ha-Sharon, Israel

[73] Assignee: Transgene S.A., Strasbourg, France

[21] Appl. No.: 479,537

[22] Filed: Jun. 7, 1995

Related U.S. Application Data

[63] Continuation of Ser. No. 403,576, Mar. 14, 1995, abandoned, which is a continuation of Ser. No. 39,320, Apr. 4, 1993, abandoned.

[30] Foreign Application Priority Data

Oct. 23, 1990 [FR] France ................................. 90 13101

[51] Int. Cl.⁶ .......................... A61K 31/70; A61K 39/00; C12N 15/86
[52] U.S. Cl. ....................... 514/44; 424/277.1; 435/320.1
[58] Field of Search .............................. 435/235.1, 320.1; 424/204.1, 232.1, 277.1; 530/300, 350; 514/44

[56] References Cited

FOREIGN PATENT DOCUMENTS

| | | |
|---|---|---|
| 0 174 534 | 3/1986 | European Pat. Off. . |
| 0 369 816 | 5/1990 | European Pat. Off. . |
| WO 88-05054 | 7/1988 | WIPO . |
| WO 89-03429 | 4/1989 | WIPO . |
| WO 90-05142 | 5/1990 | WIPO . |

OTHER PUBLICATIONS

Barnd et al. (1989) Proc. Natl. Acad. Sci. USA 86:7159.7163.
Hareuveni et al. (1990) Proc. Natl. Acad. Sci. USA 87:9498–9502.
Gendler et al. (1990) J. Biol. Chem. 265:15286–15293.
Ligtenberg et al. (1990) J. Biol. Chem. 265:5573–5578.
Hareuveni et al. (1990) Eur. J. Biochem. 189:475–486.
Wreschner et al. (1990) Eur. J. Biochem. 189:463–473.

*Primary Examiner*—George C. Elliott
*Assistant Examiner*—Robert Schwartzman
*Attorney, Agent, or Firm*—Burns, Doane, Swecker & Mathis, L.L.P.

[57] ABSTRACT

A pharmaceutical composition which comprises a recombinant vaccinia virus containing a DNA fragment encoding for a polypeptide recognized by a particular antibody H23, which recognizes a particular tumor antigen expressed on breast cancer cells is provided. The antibody specifically binds to an epitope comprising a tandem repeat sequence of 20 amino acids comprised in a transmembrane form as well as a secreted form of the POLYPEPTIDES specifically bound by antibody H23.

13 Claims, 1 Drawing Sheet

PHARMACEUTICAL COMPOSITION FOR THE TREATMENT OF A MALIGNANT TUMOR

This application is a continuation of application Ser. No. 08/403,576, filed Mar. 14, 1995, abandoned, which is a continuation of application Ser. No. 08/039,320, filed Apr. 4, 1993.

FIELD OF THE INVENTION

The present invention relates to a pharmaceutical composition intended for the curative treatment or the prevention of a malignant tumor, more especially of a carcinoma and most especially of a breast cancer.

BACKGROUND OF THE INVENTION

Most tumor cells express antigens at their surface which differ either qualitatively or quantitatively from the antigens present at the surface of the corresponding normal cells. These antigens are specific when they are expressed only by tumor cells. When they are present on both normal and tumor cells, these antigens are said to be associated with the tumor; in this case, they are present either in larger amounts or in a different form in the tumor cells.

The large majority of tumor antigens which have been characterized to date in man are human antigens associated with a tumor (hereinafter referred to as associated antigens). Among these, the following may be highlighted:

oncofetal antigens, such as carcinoembryonic antigen, which are present in fetal tissues and absent or in the trace state in the corresponding adult tissues; their expression is induced again in an aberrant manner during the development of a tumor;

differentiation antigens, which are normally expressed only during certain stages of maturation of a particular cell type; tumor cells which express such an antigen are considered to have their origin in a cell blocked in its differentiation;

the products of oncogenes which are beginning to be identified.

The specificity of an antigen associated with a tumor is hence quantitative rather than qualitative, since it may be present in a normal individual in a localized manner or intermittently (feto-embryonic period) or in the trace state, and becomes hyperexpressed (expression increased by a factor of 10 to 1000 times) only during a process of tumorigenesis. When this antigen is expressed normally, it is recognized by the immune system as part of the "Self", while its hyperexpression or its aberrant expression can trigger a humoral or cellular immune response.

Generally speaking, there are two major types of immune response: the humoral type response which is characterized by the production of antibodies by B lymphocytes, and the cell-mediated immune response which involves effector cells, i.e. essentially macrophages and cytotoxic T lymphocytes, as well as cells that regulate the immune response, i.e. helper and suppressor T lymphocytes.

A cell-mediated immune response necessitates the cooperation of helper T lymphocytes and effector cells. This cooperation takes place, in particular, as a result of interleukin-2 and various other lymphokines which are secreted by activated helper T lymphocytes. Interleukin-2 thereafter induces the action of cytotoxic T lymphocytes, and the lymphokines trigger the phagocytosis response of the macrophages. Concomitantly, there likewise exists a mechanism that suppresses the cell-mediated immune response which employs suppressor T lymphocytes.

It is now well known that patients suffering from a cancer may develop a humoral and cell-mediated immune response. This has been revealed, in particular, by demonstrating that the serum of some patients contained anti-tumor antigen antibodies, and that their serum was capable of inhibiting the growth of cancer cells in vitro. Nevertheless, inasmuch as spontaneous tumor regressions are extremely rare, it appears that the immune response observed in vitro remains ineffective in vivo. Similarly, it is also known that tumor grafts are not often rejected, even in immune animals, whereas allografts always are.

Although an immune response may develop against a tumor, it is doubtful whether it is of real benefit to the patient. Everything seems to indicate that a tumor eludes the body's mechanisms of immune surveillance. Various models have been proposed, to explain this phenomenon; for a complete and detailed review, see Scientific American, Medecine, Chapter 6, VIII Tumor Immunology, 1990. In principle, tumor antigens are considered to play a not insignificant part in modifying or diverting the immune response in favor of the tumor rather than in favor of the individual.

In the light of the complexity of the immune response against tumors and the mediocre state of current knowledge in this field, the use of an anticancer vaccine is not at all obvious. Animal studies have shown that immunization using living or killed cancer cells could lead to rejection of a subsequent tumor graft. Attempts at immunization using acellular products have generally been less successful.

To date, the possibility of manufacturing a vaccine against a cancer employing an antigen associated with this cancer hence remains controversial. A major theoretical objection to this method of treatment lies in the fact that an immune response is not considered to be sufficient to prevent or treat a tumor and that it is highly doubtful that a vaccine could be protective, that is to say capable of preventing or retarding the development of a tumor.

SUMMARY OF THE INVENTION

Nevertheless, it has now been found that a tumor antigen associated, inter alia, with breast cancer can, in vaccinal or therapeutic form, induce an immune response which protects against a subsequent tumor attack or one in the process of development. The antigen in question is, more specifically, the one recognized by the monoclonal antibody H23 derived from hybridoma ATCC No. HB 8630, deposited for the purposes of Patent Application EPA 174,534 and available to the public for experimental research work. Antibody H23 is, moreover, commercially available from Teva Pharmaceutical Industries Ltd, 5 Basel Street, Petah Tiqva, P.O. Box 1424, Tel-Aviv, Israel.

Antibody H23 was generated against particulate material present in the supernatant of in vitro cultures of the mammary tumor cell line T47D. Subsequently, it was shown that antibody H23 reacted markedly with a large majority of mammary tumor biopsies, as well as with the serum and other physiological fluids of patients with a breast cancer. In contrast, antibody H23 does not detect an antigen, or detect antigen only in the trace state, in the case of healthy individuals.

The tumor antigen recognized by antibody H23 is hence expressed in an aberrant manner by the epithelial cells of the cancerous mammary tissue in approximately 90% of cases of breast cancer whereas, in a normal individual, its expression is very low if not zero. Its presence in significant amounts has also been detected in tumoral epithelial tissues other than mammary epithelial tissues.

In a given patient, the tumor antigen recognized by antibody H23 exists in two forms: a transmembrane form and a secreted form, the amino acid sequences of which are shown, respectively, in the sequence identifiers (SI) Nos. 2 and 5. The transmembrane form and the secreted form both exhibit a high degree of polymorphism. In effect, the sequence of both forms of antigen comprises one particular subunit of 20 amino acids which may be repeated in tandem several times. The sequence of this subunit is of the formula (I)SEQ ID NO. 3: Pro-Gly-Ser-Thr-Ala-Pro-X-Ala-His-Gly-Val-Thr-Ser-Ala-Pro-Asp-Y-Arg-Pro-X in which X is Pro or Ala and Y is Thr or Asn. From one individual to another, the number of tandem repeats can vary from 20 to 80 approximately and can, inter alia, characterize the polymorphic type. Lastly, it can happen that, from one repeat to another, a minimum number of amino acids (most often 1,2 or 3 amino acids) is modified.

Moreover, it was established that the subunit of 20 amino acids described above was specific to the tumor antigen reacting with antibody H23, since this subunit contains the epitope recognized by this antibody.

Consequently, the invention provides a pharmaceutical composition intended for the curative treatment or the prevention of a malignant tumor, which comprises, as therapeutic agent, (i) a polypeptide recognized by antibody H23 or, alternatively, (ii) a virus into the genome of which a DNA fragment coding for a polypeptide recognized by antibody H23 is inserted, in combination with a diluent or vehicle which is acceptable from a pharmaceutical standpoint.

From a more general standpoint, the subject of the invention is also, as therapeutic agent for the treatment or prevention of a malignant tumor, a polypeptide recognized by antibody H23.

Similarly, the subject of the invention is also:
the use (i) of a polypeptide recognized by antibody H23, or, alternatively, the use (ii) of a virus into the genome of which a DNA fragment coding for a polypeptide recognized by antibody H23 is inserted, for treating or preventing a malignant tumor;
a method of curative treatment or prevention of a malignant tumor, which comprises the act of administering a therapeutically effective amount (i) of a polypeptide recognized by antibody H23 or, alternatively, (ii) of a virus into the genome of which a DNA fragment coding for a polypeptide recognized by antibody H23 is inserted, to a subject needing such a treatment. ("Therapeutically effective amount" is understood to mean an amount sufficient for implementing an effective therapy.)

A polypeptide recognized by antibody H23 can be, in particular, a polypeptide which comprises the sequence (I): Pro-Gly-Ser-Thr-Ala-Pro-X-Ala-His-Gly-Val-Thr-Ser-Ala-Pro-Asp-Y-Arg-Pro-X in which X is Pro or Ala and Y is Thr or Asn. The sequence (I) can be the complete sequence of the polypeptide recognized by antibody H23, or else can represent a single or repeated fragment of the polypeptide recognized by antibody H23.

A preferred polypeptide recognized by antibody H23 is a polypeptide recognized by antibody H23 whose sequence exhibits a degree of homology of at least 80%, preferably of at least 90% and, as a very special preference, from 95 to 100% inclusive with the sequence of the antigen of human epithelial tissue recognized by antibody H23 (in the text hereinafter, this antigen will be designated H23-ETA) in its transmembrane or secreted form.

As shown in SI No. 2, the transmembrane form of H23-ETA has an amino acid sequence beginning with the threonine residue at position 1 and ending with the leucine residue at position 414+(20×$\underline{n}$) whereas, as shown in SI No. 5, the secreted form of H23-ETA has an amino acid sequence beginning with the threonine residue at position 1 and ending with the proline residue at position 246+(20×$\underline{n}$). Quite generally speaking, $\underline{n}$ is a number from 1 to 80; preferably, $\underline{n}$ is a number from 1 to 40; as a very special preference, $\underline{n}$ is 2, 3 or 4.

More specifically, the transmembrane and secreted forms of H23-ETA have in common an N-terminal region of 106 amino acids (hereinafter referred to as the N-terminal region) and a middle region corresponding to the set of repeated subunits; in contrast, their C-terminal ends differ substantially. The amino acids from position 107+(20×$\underline{n}$) to position 149+(20×$\underline{n}$) are identical for both forms and vary from position 150+(20×$\underline{n}$).

A preferred polypeptide recognized by antibody H23 whose sequence is not identical to one of those described in SI Nos. 1 and 2 is characterized by at least one mutation of an amino acid (point mutation) distributed at random in the N- or C-terminal regions. The number of total mutations must, of course, satisfy the criterion of degree of homology as established above. "Point mutation" is understood to mean the deletion or substitution of an amino acid of the N- or C-terminal region described in SI No. 2 or 5, as well as the addition of an amino acid within the N- or C-terminal region described in SI No. 2 or 5.

Generally speaking, a polypeptide recognized by antibody H23 may be produced by conventional methods of chemical synthesis or else, when the amino acid sequence comprises a large number of residues, by recombinant DNA techniques. More especially, a preparation method comprises the act of culturing a host microorganism transformed with a DNA fragment coding for a polypeptide recognized by antibody H23, and the act of harvesting said polypeptide from the culture. The host organism can be any microorganism capable of being transformed, for example and without limitation, a bacterium, a yeast or alternatively a mammalian cell, insofar as the DNA fragment in question is either integrated in the genome of the host organism or inserted into a suitable expression vector, that is to say capable of replicating in the host organism. Naturally, the DNA fragment coding for the polypeptide recognized by antibody H23 is placed under the control of regions containing suitable transcription and translation signals. Expression vectors and control regions are known to a person skilled in the art.

During the last decade, the use has been proposed of recombinant viruses as agents intended for inducing an immune response against miscellaneous pathogenic organisms. To this end, adenoviruses or pox viruses are most especially suitable. For use in the present invention, avian pox viruses, canarypox virus, or vaccinia virus are highly suitable. Vaccinia virus exhibits an immune cross-reaction with smallpox virus and, as a result, has been used as an anti-smallpox vaccinal agent since the 19th century. At the beginning of the 1980s, smallpox was considered to be eradicated from the earth's surface, and the World Health Organization consequently judged it preferable to stop vaccinating against smallpox. Hence vaccinia virus is now available for use in vaccines comprising a vaccinia virus whose genome has been modified so as to express heterologous genes coding for antigenic determinants specific to a vector organism of a disease other than smallpox.

Thus, the therapeutic agent of a pharmaceutical composition according to the invention can be, alternatively, a virus into the genome of which a DNA fragment coding for a polypeptide recognized by antibody H23 has been inserted.

This type of pharmaceutical composition has the advantage of being inexpensive to produce and of great stability under miscellaneous environmental conditions. In particular, the storage conditions impose no restrictions.

The general conditions for obtaining a vaccinia virus capable of expressing a block for expression of a heterologous protein are described in European Patent EP 83,286, the content of which is incorporated herein by reference. These conditions are applicable to other viruses which are acceptable as vectors, insofar as the latter possess at least one nonessential genomic region into which an expression block may be inserted.

A vaccinia virus into the genome of which a DNA fragment coding for a polypeptide recognized by antibody H23 is inserted may also be used as a particular expression vector for the purpose of producing said polypeptide in culture of mammalian cells, as stated above.

A polypeptide recognized by antibody H23, or a virus into the genome of which a DNA fragment coding for said polypeptide is inserted, exhibits in vivo antitumor activity in the following test: C3H line mice or Fisher line rats, aged 4 to 5 weeks, are treated twice, with an interval of ten days between the two treatments, with either between 10 and 500 μg of a polypeptide recognized by antibody H23, or between $10^7$ and $10^8$ pfu (plaque forming units) of a virus into the genome of which a DNA fragment coding for said polypeptide is inserted. When a polypeptide is used, the treatment is preferably performed by subcutaneous injection. A scarification of the tail is preferable in the case of a virus. Fifteen days after the first treatment, approximately $10^4$ to $10^7$ syngeneic tumor cells expressing H23-ETA, which have been cultured in vitro, treated with trypsin, washed and resuspended in PBS (phosphate buffered saline) buffer, are injected subcutaneously in a volume of approximately 100 μl. In parallel, untreated animals are likewise subjected to an identical tumor attack. Approximately 20 days after injection of the cells, the size of the subcutaneous tumors is smaller in the animals treated with a polypeptide or a virus than in untreated animals.

A polypeptide recognized by antibody H23, or a virus into the genome of which a DNA fragment coding for said polypeptide is inserted, is, as a result, useful for the purpose of treating or preventing a cancerous condition, more especially a carcinoma type tumor (tumor developed by epithelial cells), for example a mammary tumor.

For these indications, the appropriate dosage varies in accordance, for example, with the polypeptide or virus employed, the individual being treated, the mode of administration, the use as a vaccine or as a treatment, and the nature and severity of the tumor condition which is being treated. However, in general, the indications are that satisfactory vaccination results in mammals, for example humans, may be obtained with a virus, into the genome of which a DNA fragment coding for said polypeptide is inserted, at a single dosage, or dosage repeated once or twice at intervals of approximately 1 to 3 weeks, of approximately $10^4$ pfu/kg to approximately $10^8$ pfu/kg of body weight of the mammal.

A pharmaceutical composition according to the invention may be administered by any conventional route, especially the subcutaneous route, for example in the form of an injectable solution or suspension. As a vaccine, a composition according to the invention may be administered according to the modes conventionally implemented for already known vaccines, for example in a single dose or dose repeated one or several times after a certain lapse of time. When a composition according to the invention is being used in the curative treatment of a cancer, it may be administered frequently for a sufficient period for the treatment to be effective. Such a composition may advantageously be injected intratumorally.

A pharmaceutical composition according to the invention may be prepared according to conventional techniques. When the therapeutic agent is a vaccinia virus, this virus is preferably in attenuated live form. Attenuated viral strains are available at the present time; for example, the thymidine kinase-negative Copenhagen strain. To obtain the recombinant viruses needed for using a composition according to the invention, it suffices to use such a strain. Lastly, a recombinant virus may be attenuated by a suitable chemical treatment known to a person skilled in the art.

BRIEF DESCRIPTION OF THE DRAWINGS

The invention is illustrated below, reference being made to FIG. 1.

DETAILED DESCRIPTION

EXAMPLE 1

Figure 1:
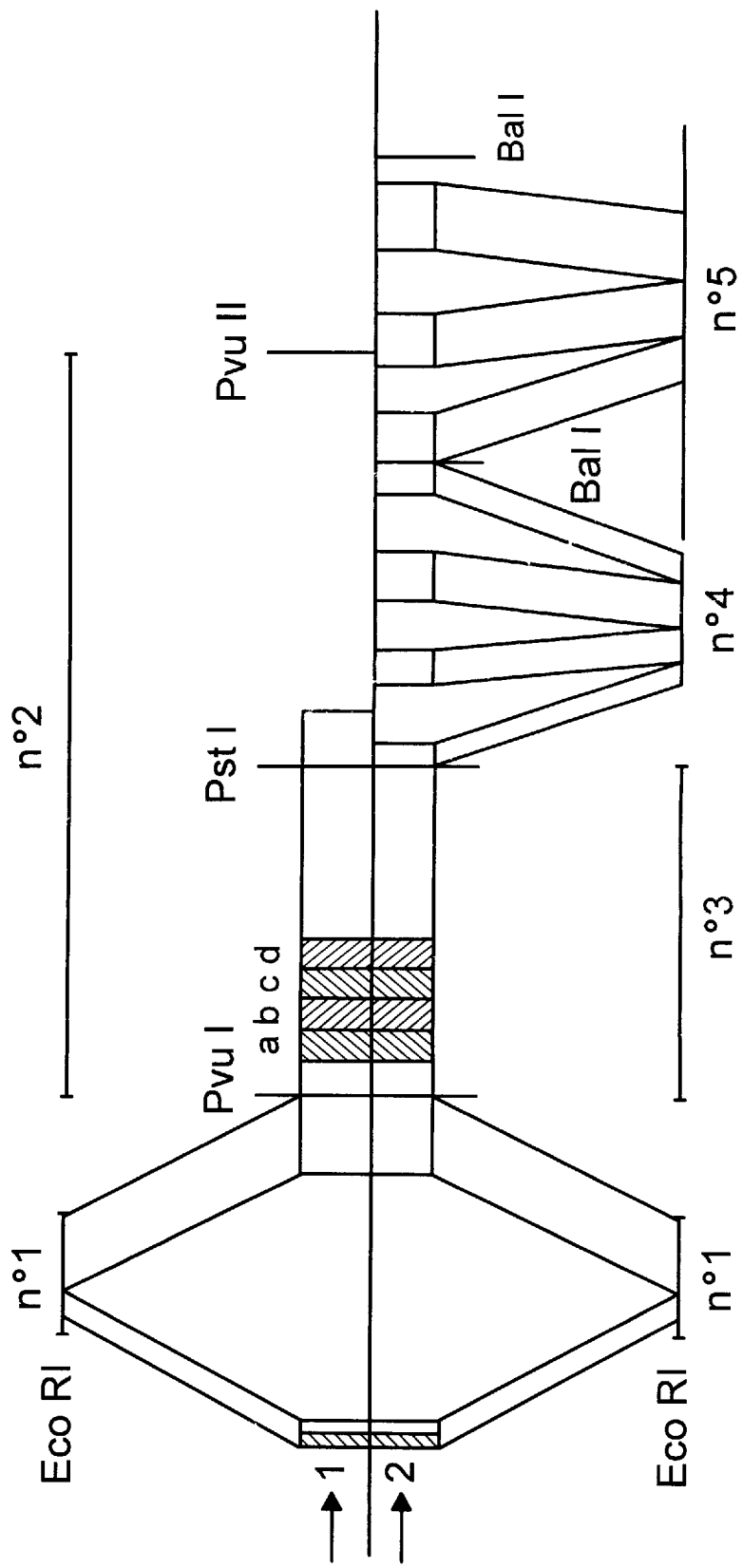
FIG. 1 shows diagrammatically a genomic DNA fragment coding for the secreted form of H23-ETA (→1) or for the transmembrane form of H23-ETA (→2). The blocks and the gaps symbolize the exons and the introns, respectively. The black background corresponds to the signal sequence and the shaded background denotes the repeat sequences (of which there are 4: a, b, c and d). The DNA fragments Nos. 1 and 2 are used for the construction of a complete fragment coding for the secreted form of H23-ETA, whereas the fragments Nos. 3 to 5 are used for constructing a complete fragment coding for the transmembrane form of H23-ETA. The restriction sites shown in this figure are also to be found in SI Nos. 1 and 2.

Complementary and genomic DNA fragments coding for portions of a polypeptide that specifically binds H23 are isolated according to the procedure described in Wreschner et al., Eur. J. Biochem, (1990) 189: 463. These fragments are thereafter used to reconstruct a DNA fragment coding for the complete H23-ETA antigen in its secreted or transmembrane form.

The plasmid constructions are described below, reference being made to FIG. 1.

A. Preparation of a vaccinia virus capable of promoting the synthesis of the secreted form of H23-ETA.

An EcoRI-PvuII complementary DNA fragment (No. 1) is introduced between the EcoRI and PvuII sites of the multiple insertion region of the vector pPolyII described in Lathe et al., Gene (1987) 57: 193 to give plasmid pETA-5'. A PvuII genomic DNA fragment (No. 2), containing 4 repeat units, is introduced into the PvuII site of the multiple insertion region of pETA-5', downstream of the fragment No. 1 and in the appropriate orientation. In the repeat units a, b, c and d, the codons $xxx_1$ and $xxx_2$ are, respectively, CCA (Pro) and CCC (Pro), CCA and CCC, GCA (Ala) and GCC, CCA and GCC. Likewise, the codon yyy is ACC (Thr) in the repeat units a, b and c; the codon yyy is AAC (Asn) in the unit d.

A BamHI-SalI fragment coding for the complete secreted form of H23-ETA is excised from the plasmid finally obtained. This fragment is then inserted between the BamHI and SalI sites of the transfer vector ptg194-poly described in Kieny et al., Bio/Technology, (1986) 4:790, downstream of the vaccinia virus promoter E7.5k and inside the vaccinia virus gene coding for thymidine kinase.

The transfer vector obtained in the above paragraph is thereafter used to transfer the block for expression of the secreted form of H23-ETA into the genome of vaccinia virus, Copenhagen strain, according to the method described in Kieny et al., Nature (1984) 312: 163. The vaccinia virus VV-ETA-S is thereby obtained.

B. Preparation of a vaccinia virus capable of promoting the synthesis of the transmembrane form of H23-ETA.

A PvuII-PstI genomic DNA fragment (No. 3), containing 4 repeat units, is introduced between the PvuII and PstI sites of the multiple insertion region of pETA-5', downstream of the fragment No. 1 and in the appropriate orientation. In the repeat units a, b, c and d, the codons $xxx_1$ and $xxx_2$ are, respectively, CCA (Pro) and CCC (Pro), CCA and CCC, GCA (Ala) and GCC, CCA and GCC. Likewise, the codon yyy is ACC (Thr) in the repeat units a, b and c; the codon yyy is AAC (Asn) in the unit d.

An EcoRI-PstI fragment corresponding to the cloned fragments is excised from the final plasmid obtained. The EcoRI cohesive end is converted to a blunt end by treatment with Klenow polymerase. This fragment is then introduced between the XhoI site, treated beforehand with Klenow polymerase, and the PstI site of the multiple insertion region of the vector pPolyII-Sfi/Not-14 described in Lathe et al., supra, to give plasmid pETA-T-5'.

A PstI-BalI complementary DNA fragment (No. 4) is introduced between the PstI and BalI sites of pETA-T-5'. A BalI-BalI complementary DNA fragment (No. 5) is then inserted into the BalI site of the plasmid finally obtained.

A BglII-SStI fragment coding for the complete transmembrane form of H23-ETA is excised from the plasmid obtained in the above paragraph; it is then introduced between the BamHI and SstI sites of the transfer vector ptg186-poly described in Kieny et al., (1986), supra, downstream of the vaccinia virus promoter E7.5k and inside the vaccinia virus gene coding for thymidine kinase.

The transfer vector obtained in the above paragraph is thereafter used to transfer the block for expression of the transmembrane form of H23-ETA into the genome of vaccinia virus, Copenhagen strain (VV-O), according to the method described in Kieny et al., (1984), supra. The vaccinia virus VV-ETA-T is thereby obtained.

EXAMPLE 2

Preparation of virus stocks.

Stocks of purified viruses are prepared using BHK-21 cells. BHK-21 cells are infected with the recombinant viruses VV-ETA-S and VV-ETA-T (0.1 pfu/cell) for 48 hours. After this time, the cultures are frozen at −20° C. and then thawed at room temperature. After destruction of the cell walls by 3 successive treatments with a "Potter" in a hypotonic buffer, the soluble proteins of the supernatant are loaded onto a cushion of 36% (w/v) sucrose and centrifuged (Beckman SW 28, 1h, 14K). The pellet containing the virus is taken up in solution in 10 mM Tris-HCl pH 8 and placed on a linear (20–40%) sucrose gradient. After centrifugation (SW 28, 40 min, 14K), the opalescent band containing the virus is withdrawn using a syringe and concentrated by centrifugation (SW 28, 20K, 1 h). The virus is lastly taken up in a small volume of 10 mM Tris-HCl pH 8 so as to obtain a viral stock assaying at approximately $10^{10}$ pfu/ml.

EXAMPLE 3

Tumor cell lines expressing H23-ETA.

A. Construction of eukaryotic plasmids capable of promoting the expression of H23-ETA.

A BamHI-SalI DNA fragment coding for the secreted form of H23-ETA is excised from the plasmid obtained in Example 1A, first paragraph. It is then reintroduced between the BamHI and SalI sites of the multiple insertion region of plasmid pHMG described in Gautier et al., Nucl. Acid Res., (1989) 17 (20): 83, so as to be placed under the control of the promoter of the 3-hydroxy-3-methylglutarylcoenzyme A reductase (HMGCR) gene, downstream of the signal sequence of SV40 polyA. Plasmid pHMG-ETA-S is thereby obtained.

Likewise, plasmid pHMG-ETA-T is constructed in a similar manner by insertion of a BamHI-EcoRV DNA fragment derived from the plasmid obtained in Example 1B, paragraph 2.

B. Preparation of cell lines.

Cells of the tumor cell line FR3T3-ras-1, obtained from Fisher rat fibroblasts by Matriceau et al., EMBO J. (1985) 4: 1435, and cells of the mouse mammary carcinoma line MM5t, derived from C3H mice, are cotransfected (i) with pHMG-ETA-S and plasmid pAG60 described in Colbere-Garapin et al., J. Mol. Biol. (1981) 150: 1 which contains a gene for resistance to Geneticin (G418) or (ii) with pHMG-ETA-T and pAG60. To accomplish the transfection, the calcium phosphate precipitation method of Graham et al., Virology (1973) 52: 456 modified by Wigler et al., Cell (1978) 14: 725 is used.

The transfected clones are selected in the presence of 500 μl/ml of G418 and are thereafter cultured. Selection of the clones expressing H23-ETA is accomplished by labelling the cells with peroxidase after reaction with antibody H23. Cell lines in the pure state are obtained by the limiting dilution method, and the expression of H23-ETA is monitored.

The cell lines are designated as follows:

FR3T3-ras-1 (pAG60/pHMG-ETA-S): F-S
FR3T3-ras-1 (pAG60/pHMG-ETA-T): F-T
FR3T3-ras-1 (pAG60/pHMG): F-C
MM5tC3H (pAG60/pHMG-ETA-S): M-S
MM5tC3H (pAG60/pHMG-ETA-T): M-T
MM5tC3H (pAG60/pHMG): M-C

EXAMPLE 4

Demonstration of the vaccinal effect of H23-ETA.

Fisher IOPS line male and female rats and C3H line female mice aged 4 to 5 weeks are immunized in the following manner: a purified viral preparation of VV-ETA-S, VV-ETA-T or VV-O is administered to the animals, by scarification of the tail, in a volume of 10 μl corresponding to approximately $2\times10^7$ pfu. This treatment is repeated 10 days later.

The F-S, F-T, F-C, M-S, M-T and M-C tumor lines are cultured in modified Dulbecco medium (Gibco) supplemented with 10% of fetal calf serum, 100 units of penicillin and 100 μg/ml of streptomycin. The cultures are then treated with trypsin, washed and suspended in PBS (phosphate buffered saline) buffer.

14 days after the first stage of immunization, $2 \times 10^4$ F-C cells, $4 \times 10^4$ F-S cells, $1.5 \times 10^5$ F-T cells or $2 \times 10^6$ M-C, M-S or M-T cells are injected subcutaneously into an animal in a volume of 100 µl.

The appearance of the subcutaneous tumors is monitored daily. The diameter of the tumors is measured in two dimensions. The complete data for the experiment and the results are presented in Table I below:

TABLE I

| Animal | Virus | Tumor cells | Number of animals having a tumor nodule relative to the total number of animals treated | Measured average diameter of the tumor nodules (in mm) × days after injection of the cells | Percentage of animals free from tumors |
|---|---|---|---|---|---|
| Fisher line male rats | | F-C | 4/4 | 31 (20 days) | 0 |
| | | F-S | 3/4 | 25 (25 days) | 25 |
| | | F-T | 3/6 | 25 (30 days) | 50 |
| | VV-ETA-S | F-C | 8/8 | 40 (20 days) | 0 |
| | | F-S | 3/8 | 7.5 (25 days) | 62.5 |
| | | F-T | 1/8 | 0.87 (30 days) | 87.5 |
| | VV-ETA-T | F-C | 8/8 | 32 (20 days) | 0 |
| | | F-S | 1/8 | 0.38 (25 days) | 87.5 |
| | | F-T | 0/8 | 0 (30 days) | 100 |
| | | F-S | 10/10 | 11.2 (20 days) | 0 |
| | | F-T | 10/10 | 25 (20 days) | 0 |
| | VV-ETA-S | F-S | 9/10 | 16 (20 days) | 10 |
| | | F-T | 9/10 | 30 (20 days) | 10 |
| | VV-ETA-T | F-S | 5/10 | 1.7 (20 days) | 50 |
| | | F-T | 5/10 | 2.8 (20 days) | 50 |
| Fisher line female rats | VV-O | F-S | 10/10 | 19.8 (20 days) | 0 |
| | | F-T | 10/10 | 28 (20 days) | 0 |
| | VV-ETA-S | F-S | 8/10 | 10.6 (20 days) | 20 |
| | | F-T | 9/9 | 33.8 (20 days) | 0 |
| | VV-ETA-T | F-S | 5/10 | 0.1 (25 days) | 50 |
| | | F-T | 1/10 | | 90 |

Table I shows that, when the animals are subjected to infection with F-S or F-T, the incidence of appearance of tumors in a group of animals treated beforehand using the vaccinia virus VV-ETA-S or VV-ETA-T is lower than in the groups of untreated animals or animals treated with a VV-O vaccinia virus. Moreover, the size of the tumor nodules which appear in animals treated beforehand with VV-ETA-S or VV-ETA-T is much smaller than that of the tumor nodules observed in the untreated animals or animals treated with VV-O.

Immunization using VV-ETA-S or VV-ETA-T is effective only in the case of tumors induced with cells expressing the secreted or transmembrane form of H23-ETA. The vaccinal effect of the viruses is hence very specific.

Lastly, the vaccinal effect of VV-ETA-T appears to be superior to that of VV-ETA-S, irrespective of the form of H23-ETA expressed by the cells inducing the tumors.

EXAMPLE 5

Demonstration of the curative effect of H23-ETA.

Fisher line rats are infected with tumor cells as described in Example 4. As soon as tumors have appeared (10 to 15 days later), treatment is carried out using the viral preparations, as described in Example 4.

The data and results of the experiment are presented in Table II below:

TABLE II

| | | Number of animals having a tumor nodule relative to the total number of animals treated | | Measured average diameter of the tumors (in mm) | |
|---|---|---|---|---|---|
| Virus | Tumor cells | 25 days after injection | 50 days after injection | 25 days after injection | 50 days after injection |
| VV-O | F-S | 10/10 | 10/10 | 27.8 | all dead |
| | F-T | 10/10 | 10/10 | 27.7 | all dead |
| VV-ETA-S | F-S | 10/10 | 10/10 | 31.5 | all dead |
| | F-T | 9/10 | 7/10 | 15.5 | 8.5 |
| VV-ETA-T | F-S | 9/10 | 10/10 | 26.8 | 50.2 |
| | F-T | 7/10 | 7/10 | 11.6 | 9.4 |

Table II shows that the treatment of an infection with VV-ETA-S or VV-ETA-T has a favorable effect on the incidence of appearance and the size of the tumors relative to the control test. Moreover, VV-ETA-T appears to be more effective than VV-ETA-S.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 6192 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: sig_peptide
        ( B ) LOCATION: 58..120

( i x ) FEATURE:
        ( A ) NAME/KEY: repeat_region
        ( B ) LOCATION: 439..5239
        ( D ) OTHER INFORMATION: /note= "The nucleotides spanning
            439-5239 constitute a repeated region wherein the repeat
            is 60 nucleotides and encodes 20 amino acids, 17 of
            which are fixed. The number of such repeats varies from
            1 to 80."

( i x ) FEATURE:
        ( A ) NAME/KEY: mat_peptide
        ( B ) LOCATION: 121..6166

( i x ) FEATURE:
        ( A ) NAME/KEY: repeat_region
        ( B ) LOCATION: 457
        ( D ) OTHER INFORMATION: /note= "Nucleotide 457 is X1 = NNN
            which is the codon for Pro or Ala wherein Pro = CCT, CCC,
            CCA, or CCG; and Ala = GCT, GCC, GCA, or GCG."

( i x ) FEATURE:
        ( A ) NAME/KEY: repeat_region
        ( B ) LOCATION: 487
        ( D ) OTHER INFORMATION: /note= "Nucleotide 487 is Y = NNN
            which is the codon for Thr or Asn wherein Thr = ACT, ACC,
            ACA, or ACG; and Asn = AAT or AAC."

( i x ) FEATURE:
        ( A ) NAME/KEY: repeat_region
        ( B ) LOCATION: 496
        ( D ) OTHER INFORMATION: /note= "Nucleotide 496 is X2 = NNN
            which is the codon for Pro or Ala wherein Pro = CCT, CCC,
            CCA, or CCG; and Ala = GCT, GCC, GCA, or GCG."

( x i ) SEQUENCE DESCRIPTION: SEQ ID NO:1:

```
GAATTCCCTG  GCTGCTTGAA  TCTGTTCTGC  CCCCTCCCCA  CCCATTTCAC  CACCACCATG    60

ACACCGGGCA  CCCAGTCTCC  TTTCTTCCTG  CTGCTGCTCC  TCACAGTGCT  TACAGTTGTT   120

ACAGGTTCTG  GTCATGCAAG  CTCTACCCCA  GGTGGAGAAA  AGGAGACTTC  GGCTACCCAG   180

AGAAGTTCAG  TGCCCAGCTC  TACTGAGAAG  AATGCTGTGA  GTATGACCAG  CAGCGTACTC   240

TCCAGCCACA  GCCCCGGTTC  AGGCTCCTCC  ACCACTCAGG  GACAGGATGT  CACTCTGGCC   300

CCGGCCACGG  AACCAGCTTC  AGGTTCAGCT  GCCACCTGGG  GACAGGATGT  CACCTCGGTC   360

CCAGTCACCA  GGCCAGCCCT  GGGCTCCACC  ACCCCGCCAG  CCACGATGT   CACCTCAGCC   420

CCGGACAACA  AGCCAGCCCC  GGGCTCCACC  GCCCCNNNG   CCCACGGTGT  CACCTCGGCC   480

CCGGACNNNA  GGCCGNNNCC  GGGCTCCACC  GCCCCNNNG   CCCACGGTGT  CACCTCGGCC   540

CCGGACNNNA  GGCCGNNNCC  GGGCTCCACC  GCCCCNNNG   CCCACGGTGT  CACCTCGGCC   600

CCGGACNNNA  GGCCGNNNCC  GGGCTCCACC  GCCCCNNNG   CCCACGGTGT  CACCTCGGCC   660
```

| | | | | | | |
|---|---|---|---|---|---|---|
| CCGGACNNNA | GGCCGNNNCC | GGGCTCCACC | GCCCCCNNNG | CCCACGGTGT | CACCTCGGCC | 720 |
| CCGGACNNNA | GGCCGNNNCC | GGGCTCCACC | GCCCCCNNNG | CCCACGGTGT | CACCTCGGCC | 780 |
| CCGGACNNNA | GGCCGNNNCC | GGGCTCCACC | GCCCCCNNNG | CCCACGGTGT | CACCTCGGCC | 840 |
| CCGGACNNNA | GGCCGNNNCC | GGGCTCCACC | GCCCCCNNNG | CCCACGGTGT | CACCTCGGCC | 900 |
| CCGGACNNNA | GGCCGNNNCC | GGGCTCCACC | GCCCCCNNNG | CCCACGGTGT | CACCTCGGCC | 960 |
| CCGGACNNNA | GGCCGNNNCC | GGGCTCCACC | GCCCCCNNNG | CCCACGGTGT | CACCTCGGCC | 1020 |
| CCGGACNNNA | GGCCGNNNCC | GGGCTCCACC | GCCCCCNNNG | CCCACGGTGT | CACCTCGGCC | 1080 |
| CCGGACNNNA | GGCCGNNNCC | GGGCTCCACC | GCCCCCNNNG | CCCACGGTGT | CACCTCGGCC | 1140 |
| CCGGACNNNA | GGCCGNNNCC | GGGCTCCACC | GCCCCCNNNG | CCCACGGTGT | CACCTCGGCC | 1200 |
| CCGGACNNNA | GGCCGNNNCC | GGGCTCCACC | GCCCCCNNNG | CCCACGGTGT | CACCTCGGCC | 1260 |
| CCGGACNNNA | GGCCGNNNCC | GGGCTCCACC | GCCCCCNNNG | CCCACGGTGT | CACCTCGGCC | 1320 |
| CCGGACNNNA | GGCCGNNNCC | GGGCTCCACC | GCCCCCNNNG | CCCACGGTGT | CACCTCGGCC | 1380 |
| CCGGACNNNA | GGCCGNNNCC | GGGCTCCACC | GCCCCCNNNG | CCCACGGTGT | CACCTCGGCC | 1440 |
| CCGGACNNNA | GGCCGNNNCC | GGGCTCCACC | GCCCCCNNNG | CCCACGGTGT | CACCTCGGCC | 1500 |
| CCGGACNNNA | GGCCGNNNCC | GGGCTCCACC | GCCCCCNNNG | CCCACGGTGT | CACCTCGGCC | 1560 |
| CCGGACNNNA | GGCCGNNNCC | GGGCTCCACC | GCCCCCNNNG | CCCACGGTGT | CACCTCGGCC | 1620 |
| CCGGACNNNA | GGCCGNNNCC | GGGCTCCACC | GCCCCCNNNG | CCCACGGTGT | CACCTCGGCC | 1680 |
| CCGGACNNNA | GGCCGNNNCC | GGGCTCCACC | GCCCCCNNNG | CCCACGGTGT | CACCTCGGCC | 1740 |
| CCGGACNNNA | GGCCGNNNCC | GGGCTCCACC | GCCCCCNNNG | CCCACGGTGT | CACCTCGGCC | 1800 |
| CCGGACNNNA | GGCCGNNNCC | GGGCTCCACC | GCCCCCNNNG | CCCACGGTGT | CACCTCGGCC | 1860 |
| CCGGACNNNA | GGCCGNNNCC | GGGCTCCACC | GCCCCCNNNG | CCCACGGTGT | CACCTCGGCC | 1920 |
| CCGGACNNNA | GGCCGNNNCC | GGGCTCCACC | GCCCCCNNNG | CCCACGGTGT | CACCTCGGCC | 1980 |
| CCGGACNNNA | GGCCGNNNCC | GGGCTCCACC | GCCCCCNNNG | CCCACGGTGT | CACCTCGGCC | 2040 |
| CCGGACNNNA | GGCCGNNNCC | GGGCTCCACC | GCCCCCNNNG | CCCACGGTGT | CACCTCGGCC | 2100 |
| CCGGACNNNA | GGCCGNNNCC | GGGCTCCACC | GCCCCCNNNG | CCCACGGTGT | CACCTCGGCC | 2160 |
| CCGGACNNNA | GGCCGNNNCC | GGGCTCCACC | GCCCCCNNNG | CCCACGGTGT | CACCTCGGCC | 2220 |
| CCGGACNNNA | GGCCGNNNCC | GGGCTCCACC | GCCCCCNNNG | CCCACGGTGT | CACCTCGGCC | 2280 |
| CCGGACNNNA | GGCCGNNNCC | GGGCTCCACC | GCCCCCNNNG | CCCACGGTGT | CACCTCGGCC | 2340 |
| CCGGACNNNA | GGCCGNNNCC | GGGCTCCACC | GCCCCCNNNG | CCCACGGTGT | CACCTCGGCC | 2400 |
| CCGGACNNNA | GGCCGNNNCC | GGGCTCCACC | GCCCCCNNNG | CCCACGGTGT | CACCTCGGCC | 2460 |
| CCGGACNNNA | GGCCGNNNCC | GGGCTCCACC | GCCCCCNNNG | CCCACGGTGT | CACCTCGGCC | 2520 |
| CCGGACNNNA | GGCCGNNNCC | GGGCTCCACC | GCCCCCNNNG | CCCACGGTGT | CACCTCGGCC | 2580 |
| CCGGACNNNA | GGCCGNNNCC | GGGCTCCACC | GCCCCCNNNG | CCCACGGTGT | CACCTCGGCC | 2640 |
| CCGGACNNNA | GGCCGNNNCC | GGGCTCCACC | GCCCCCNNNG | CCCACGGTGT | CACCTCGGCC | 2700 |
| CCGGACNNNA | GGCCGNNNCC | GGGCTCCACC | GCCCCCNNNG | CCCACGGTGT | CACCTCGGCC | 2760 |
| CCGGACNNNA | GGCCGNNNCC | GGGCTCCACC | GCCCCCNNNG | CCCACGGTGT | CACCTCGGCC | 2820 |
| CCGGACNNNA | GGCCGNNNCC | GGGCTCCACC | GCCCCCNNNG | CCCACGGTGT | CACCTCGGCC | 2880 |
| CCGGACNNNA | GGCCGNNNCC | GGGCTCCACC | GCCCCCNNNG | CCCACGGTGT | CACCTCGGCC | 2940 |
| CCGGACNNNA | GGCCGNNNCC | GGGCTCCACC | GCCCCCNNNG | CCCACGGTGT | CACCTCGGCC | 3000 |
| CCGGACNNNA | GGCCGNNNCC | GGGCTCCACC | GCCCCCNNNG | CCCACGGTGT | CACCTCGGCC | 3060 |

| | | | | | | |
|---|---|---|---|---|---|---|
| CCGGACNNNA | GGCCGNNNCC | GGGCTCCACC | GCCCCCNNNG | CCCACGGTGT | CACCTCGGCC | 3120 |
| CCGGACNNNA | GGCCGNNNCC | GGGCTCCACC | GCCCCCNNNG | CCCACGGTGT | CACCTCGGCC | 3180 |
| CCGGACNNNA | GGCCGNNNCC | GGGCTCCACC | GCCCCCNNNG | CCCACGGTGT | CACCTCGGCC | 3240 |
| CCGGACNNNA | GGCCGNNNCC | GGGCTCCACC | GCCCCCNNNG | CCCACGGTGT | CACCTCGGCC | 3300 |
| CCGGACNNNA | GGCCGNNNCC | GGGCTCCACC | GCCCCCNNNG | CCCACGGTGT | CACCTCGGCC | 3360 |
| CCGGACNNNA | GGCCGNNNCC | GGGCTCCACC | GCCCCCNNNG | CCCACGGTGT | CACCTCGGCC | 3420 |
| CCGGACNNNA | GGCCGNNNCC | GGGCTCCACC | GCCCCCNNNG | CCCACGGTGT | CACCTCGGCC | 3480 |
| CCGGACNNNA | GGCCGNNNCC | GGGCTCCACC | GCCCCCNNNG | CCCACGGTGT | CACCTCGGCC | 3540 |
| CCGGACNNNA | GGCCGNNNCC | GGGCTCCACC | GCCCCCNNNG | CCCACGGTGT | CACCTCGGCC | 3600 |
| CCGGACNNNA | GGCCGNNNCC | GGGCTCCACC | GCCCCCNNNG | CCCACGGTGT | CACCTCGGCC | 3660 |
| CCGGACNNNA | GGCCGNNNCC | GGGCTCCACC | GCCCCCNNNG | CCCACGGTGT | CACCTCGGCC | 3720 |
| CCGGACNNNA | GGCCGNNNCC | GGGCTCCACC | GCCCCCNNNG | CCCACGGTGT | CACCTCGGCC | 3780 |
| CCGGACNNNA | GGCCGNNNCC | GGGCTCCACC | GCCCCCNNNG | CCCACGGTGT | CACCTCGGCC | 3840 |
| CCGGACNNNA | GGCCGNNNCC | GGGCTCCACC | GCCCCCNNNG | CCCACGGTGT | CACCTCGGCC | 3900 |
| CCGGACNNNA | GGCCGNNNCC | GGGCTCCACC | GCCCCCNNNG | CCCACGGTGT | CACCTCGGCC | 3960 |
| CCGGACNNNA | GGCCGNNNCC | GGGCTCCACC | GCCCCCNNNG | CCCACGGTGT | CACCTCGGCC | 4020 |
| CCGGACNNNA | GGCCGNNNCC | GGGCTCCACC | GCCCCCNNNG | CCCACGGTGT | CACCTCGGCC | 4080 |
| CCGGACNNNA | GGCCGNNNCC | GGGCTCCACC | GCCCCCNNNG | CCCACGGTGT | CACCTCGGCC | 4140 |
| CCGGACNNNA | GGCCGNNNCC | GGGCTCCACC | GCCCCCNNNG | CCCACGGTGT | CACCTCGGCC | 4200 |
| CCGGACNNNA | GGCCGNNNCC | GGGCTCCACC | GCCCCCNNNG | CCCACGGTGT | CACCTCGGCC | 4260 |
| CCGGACNNNA | GGCCGNNNCC | GGGCTCCACC | GCCCCCNNNG | CCCACGGTGT | CACCTCGGCC | 4320 |
| CCGGACNNNA | GGCCGNNNCC | GGGCTCCACC | GCCCCCNNNG | CCCACGGTGT | CACCTCGGCC | 4380 |
| CCGGACNNNA | GGCCGNNNCC | GGGCTCCACC | GCCCCCNNNG | CCCACGGTGT | CACCTCGGCC | 4440 |
| CCGGACNNNA | GGCCGNNNCC | GGGCTCCACC | GCCCCCNNNG | CCCACGGTGT | CACCTCGGCC | 4500 |
| CCGGACNNNA | GGCCGNNNCC | GGGCTCCACC | GCCCCCNNNG | CCCACGGTGT | CACCTCGGCC | 4560 |
| CCGGACNNNA | GGCCGNNNCC | GGGCTCCACC | GCCCCCNNNG | CCCACGGTGT | CACCTCGGCC | 4620 |
| CCGGACNNNA | GGCCGNNNCC | GGGCTCCACC | GCCCCCNNNG | CCCACGGTGT | CACCTCGGCC | 4680 |
| CCGGACNNNA | GGCCGNNNCC | GGGCTCCACC | GCCCCCNNNG | CCCACGGTGT | CACCTCGGCC | 4740 |
| CCGGACNNNA | GGCCGNNNCC | GGGCTCCACC | GCCCCCNNNG | CCCACGGTGT | CACCTCGGCC | 4800 |
| CCGGACNNNA | GGCCGNNNCC | GGGCTCCACC | GCCCCCNNNG | CCCACGGTGT | CACCTCGGCC | 4860 |
| CCGGACNNNA | GGCCGNNNCC | GGGCTCCACC | GCCCCCNNNG | CCCACGGTGT | CACCTCGGCC | 4920 |
| CCGGACNNNA | GGCCGNNNCC | GGGCTCCACC | GCCCCCNNNG | CCCACGGTGT | CACCTCGGCC | 4980 |
| CCGGACNNNA | GGCCGNNNCC | GGGCTCCACC | GCCCCCNNNG | CCCACGGTGT | CACCTCGGCC | 5040 |
| CCGGACNNNA | GGCCGNNNCC | GGGCTCCACC | GCCCCCNNNG | CCCACGGTGT | CACCTCGGCC | 5100 |
| CCGGACNNNA | GGCCGNNNCC | GGGCTCCACC | GCCCCCNNNG | CCCACGGTGT | CACCTCGGCC | 5160 |
| CCGGACNNNA | GGCCGNNNCC | GGGCTCCACC | GCCCCCNNNG | CCCACGGTGT | CACCTCGGCC | 5220 |
| CCGGACNNNA | GGCCGNNNTT | GGGCTCCACC | GCCCCTCCAG | TCCACAATGT | CACCTCGGCC | 5280 |
| TCAGGCTCTG | CATCAGGCTC | AGCTTCTACT | CTGGTGCACA | ACGGCACCTC | TGCCAGGGCT | 5340 |
| ACCACAACCC | CAGCCAGCAA | GAGCACTCCA | CCCAGCATTC | CCAGCCACCA | CTCTGATACT | 5400 |
| CCTACCACCC | TTGCCAGCCA | TAGCACCAAG | ACTGATGCCA | GTAGCACTCA | CCATAGCACG | 5460 |

| | | | | | |
|---|---|---|---|---|---|
| GTACCTCCTC | TCACCTCCTC | CAATCACAGC | ACTTCTCCCC | AGTTGTCTAC | TGGGGTCTCT | 5520
| TTCTTTTTCC | TGTCTTTTCA | CATTTCAAAC | CTCCAGTTTA | ATTCCTCTCT | GGAAGATCCC | 5580
| AGCACCGACT | ACTACCAAGA | GCTGCAGAGA | GACATTTCTG | AAATGTTTTT | GCAGAATTAT | 5640
| AAACAAGGGG | GTTTTCTGGG | CCTCTCCAAT | ATTAAGTTCA | GGCCAGAATC | TGTGGTGGTA | 5700
| CAATTGACTC | TGGCCTTCCG | AGAAGGTACC | ATCAATGTCC | ACGACGTGGA | GACACAGTTC | 5760
| AATCAGTATA | AAACGGAAGC | AGCCTCTCGA | TATAACCTGA | CGATCTCAGA | CGTCAGCGTG | 5820
| AGTCATGTGC | CATTTCCTTT | CTCTGCCCAG | TCTGGGGCTG | GGGTGCCAGG | CTGGGGCATC | 5880
| GCGCTGCTGG | TGCTGGTCTG | TGTTCTGGTT | GCGCTGGCCA | TTGTCTATCT | CATTGCCTTG | 5940
| GCTGTCTGTC | AGTGCCGCCG | AAAGAACTAC | GGGCAGCTGG | ACATCTTTCC | AGCCCGGGAT | 6000
| ACCTACCATC | CTATGAGCGA | GTACCCCACC | TACCACACCC | ATGGGCGCTA | TGTGCCCCCT | 6060
| AGCAGTACCG | ATCGTAGCCC | CTATGAGAAG | GTTTCTGCAG | GTAATGGTGG | CAGCAGCCTC | 6120
| TCTTACACAA | ACCCAGCAGT | GGCAGCCACT | TCTGCCAACT | TGTAGGGGCA | CGTCGCCCTC | 6180
| TGAGCTGAGT | GG | | | | | 6192

( 2 ) INFORMATION FOR SEQ ID NO:2:

( i ) SEQUENCE CHARACTERISTICS:
        ( A ) LENGTH: 2035 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 128..1899
        ( D ) OTHER INFORMATION: /note= "The amino acids spanning
        128 to 1899 constitute a repeated region wherein the
        repeat is 20 amino acids, 17 of which are fixed. The
        number of such repeats varies from 1 to 40."

( i x ) FEATURE:
        ( A ) NAME/KEY: Peptide
        ( B ) LOCATION: 134
        ( D ) OTHER INFORMATION: /note= "Amino acid 134 is X1 = Xaa
        Xaa Xaa which is the codon for Pro or Ala wherein
        Pro =CCT, CCC, CCA, or CCG; and Ala = GCT, GCC, GCA,
        or GCG."

( i x ) FEATURE:
        ( A ) NAME/KEY: Peptide
        ( B ) LOCATION: 144
        ( D ) OTHER INFORMATION: /note= "Amino acid 144 is Y = Xaa
        which is the codon for Thr or Asn wherein Thr = ACT, ACC,
        ACA, or ACG; and Asn = AAT or AAC."

( i x ) FEATURE:
        ( A ) NAME/KEY: Peptide
        ( B ) LOCATION: 147
        ( D ) OTHER INFORMATION: /note= "Amino acid 147 is X2 = Xaa
        which is the codon for Pro or Ala wherein Pro = CCT, CCC,
        CCA, or CCG; and Ala = GCT, GCC, GCA, or GCG."

( i x ) FEATURE:
        ( A ) NAME/KEY: Peptide
        ( B ) LOCATION: 1..21
        ( D ) OTHER INFORMATION: /note= "Amino acids 1 to 21 are a
        21 amino acid precursor sequence."

( x i ) SEQUENCE DESCRIPTION: SEQ ID NO:2:

```
Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
                20                  25                  30
```

-continued

```
Gly  Glu  Lys  Glu  Thr  Ser  Ala  Thr  Gln  Arg  Ser  Ser  Val  Pro  Ser  Ser
          35                      40                      45

Thr  Glu  Lys  Asn  Ala  Val  Ser  Met  Thr  Ser  Ser  Val  Leu  Ser  Ser  His
     50                      55                      60

Ser  Pro  Gly  Ser  Gly  Ser  Ser  Thr  Thr  Gln  Gly  Gln  Asp  Val  Thr  Leu
65                       70                      75                       80

Ala  Pro  Ala  Thr  Glu  Pro  Ala  Ser  Gly  Ser  Ala  Ala  Thr  Trp  Gly  Gln
                    85                       90                      95

Asp  Val  Thr  Ser  Val  Pro  Val  Thr  Arg  Pro  Ala  Leu  Gly  Ser  Thr  Thr
               100                 105                      110

Pro  Pro  Ala  His  Asp  Val  Thr  Ser  Ala  Pro  Asp  Asn  Lys  Pro  Ala  Pro
               115                 120                 125

Gly  Ser  Thr  Ala  Pro  Xaa  Ala  His  Gly  Val  Thr  Ser  Ala  Pro  Asp  Xaa
     130                 135                      140

Arg  Pro  Xaa  Pro  Gly  Ser  Thr  Ala  Pro  Xaa  Ala  His  Gly  Val  Thr  Ser
145                      150                      155                      160

Ala  Pro  Asp  Xaa  Arg  Pro  Xaa  Pro  Gly  Ser  Thr  Ala  Pro  Xaa  Ala  His
               165                      170                      175

Gly  Val  Thr  Ser  Ala  Pro  Asp  Xaa  Arg  Pro  Xaa  Pro  Gly  Ser  Thr  Ala
               180                 185                      190

Pro  Xaa  Ala  His  Gly  Val  Thr  Ser  Ala  Pro  Asp  Xaa  Arg  Pro  Xaa  Pro
          195                      200                 205

Gly  Ser  Thr  Ala  Pro  Xaa  Ala  His  Gly  Val  Thr  Ser  Ala  Pro  Asp  Xaa
     210                 215                      220

Arg  Pro  Xaa  Pro  Gly  Ser  Thr  Ala  Pro  Xaa  Ala  His  Gly  Val  Thr  Ser
225                      230                      235                      240

Ala  Pro  Asp  Xaa  Arg  Pro  Xaa  Pro  Gly  Ser  Thr  Ala  Pro  Xaa  Ala  His
               245                      250                      255

Gly  Val  Thr  Ser  Ala  Pro  Asp  Xaa  Arg  Pro  Xaa  Pro  Gly  Ser  Thr  Ala
               260                 265                      270

Pro  Xaa  Ala  His  Gly  Val  Thr  Ser  Ala  Pro  Asp  Xaa  Arg  Pro  Xaa  Pro
          275                      280                 285

Gly  Ser  Thr  Ala  Pro  Xaa  Ala  His  Gly  Val  Thr  Ser  Ala  Pro  Asp  Xaa
     290                 295                      300

Arg  Pro  Xaa  Pro  Gly  Ser  Thr  Ala  Pro  Xaa  Ala  His  Gly  Val  Thr  Ser
305                      310                      315                      320

Ala  Pro  Asp  Xaa  Arg  Pro  Xaa  Pro  Gly  Ser  Thr  Ala  Pro  Xaa  Ala  His
               325                      330                      335

Gly  Val  Thr  Ser  Ala  Pro  Asp  Xaa  Arg  Pro  Xaa  Pro  Gly  Ser  Thr  Ala
               340                 345                      350

Pro  Xaa  Ala  His  Gly  Val  Thr  Ser  Ala  Pro  Asp  Xaa  Arg  Pro  Xaa  Pro
          355                      360                 365

Gly  Ser  Thr  Ala  Pro  Xaa  Ala  His  Gly  Val  Thr  Ser  Ala  Pro  Asp  Xaa
     370                 375                      380

Arg  Pro  Xaa  Pro  Gly  Ser  Thr  Ala  Pro  Xaa  Ala  His  Gly  Val  Thr  Ser
385                      390                      395                      400

Ala  Pro  Asp  Xaa  Arg  Pro  Xaa  Pro  Gly  Ser  Thr  Ala  Pro  Xaa  Ala  His
               405                      410                      415

Gly  Val  Thr  Ser  Ala  Pro  Asp  Xaa  Arg  Pro  Xaa  Pro  Gly  Ser  Thr  Ala
               420                 425                      430

Pro  Xaa  Ala  His  Gly  Val  Thr  Ser  Ala  Pro  Asp  Xaa  Arg  Pro  Xaa  Pro
          435                      440                 445
```

```
Gly  Ser  Thr  Ala  Pro  Xaa  Ala  His  Gly  Val  Thr  Ser  Ala  Pro  Asp  Xaa
     450                 455                      460

Arg  Pro  Xaa  Pro  Gly  Ser  Thr  Ala  Pro  Xaa  Ala  His  Gly  Val  Thr  Ser
465            470                      475                           480

Ala  Pro  Asp  Xaa  Arg  Pro  Xaa  Pro  Gly  Ser  Thr  Ala  Pro  Xaa  Ala  His
               485                      490                           495

Gly  Val  Thr  Ser  Ala  Pro  Asp  Xaa  Arg  Pro  Xaa  Pro  Gly  Ser  Thr  Ala
               500                 505                      510

Pro  Xaa  Ala  His  Gly  Val  Thr  Ser  Ala  Pro  Asp  Xaa  Arg  Pro  Xaa  Pro
          515                 520                      525

Gly  Ser  Thr  Ala  Pro  Xaa  Ala  His  Gly  Val  Thr  Ser  Ala  Pro  Asp  Xaa
     530                 535                      540

Arg  Pro  Xaa  Pro  Gly  Ser  Thr  Ala  Pro  Xaa  Ala  His  Gly  Val  Thr  Ser
545            550                      555                           560

Ala  Pro  Asp  Xaa  Arg  Pro  Xaa  Pro  Gly  Ser  Thr  Ala  Pro  Xaa  Ala  His
               565                      570                           575

Gly  Val  Thr  Ser  Ala  Pro  Asp  Xaa  Arg  Pro  Xaa  Pro  Gly  Ser  Thr  Ala
               580                 585                      590

Pro  Xaa  Ala  His  Gly  Val  Thr  Ser  Ala  Pro  Asp  Xaa  Arg  Pro  Xaa  Pro
          595                 600                      605

Gly  Ser  Thr  Ala  Pro  Xaa  Ala  His  Gly  Val  Thr  Ser  Ala  Pro  Asp  Xaa
     610                 615                      620

Arg  Pro  Xaa  Pro  Gly  Ser  Thr  Ala  Pro  Xaa  Ala  His  Gly  Val  Thr  Ser
625            630                      635                           640

Ala  Pro  Asp  Xaa  Arg  Pro  Xaa  Pro  Gly  Ser  Thr  Ala  Pro  Xaa  Ala  His
               645                      650                           655

Gly  Val  Thr  Ser  Ala  Pro  Asp  Xaa  Arg  Pro  Xaa  Pro  Gly  Ser  Thr  Ala
               660                 665                      670

Pro  Xaa  Ala  His  Gly  Val  Thr  Ser  Ala  Pro  Asp  Xaa  Arg  Pro  Xaa  Pro
          675                 680                      685

Gly  Ser  Thr  Ala  Pro  Xaa  Ala  His  Gly  Val  Thr  Ser  Ala  Pro  Asp  Xaa
     690                 695                      700

Arg  Pro  Xaa  Pro  Gly  Ser  Thr  Ala  Pro  Xaa  Ala  His  Gly  Val  Thr  Ser
705            710                      715                           720

Ala  Pro  Asp  Xaa  Arg  Pro  Xaa  Pro  Gly  Ser  Thr  Ala  Pro  Xaa  Ala  His
               725                      730                           735

Gly  Val  Thr  Ser  Ala  Pro  Asp  Xaa  Arg  Pro  Xaa  Pro  Gly  Ser  Thr  Ala
               740                 745                      750

Pro  Xaa  Ala  His  Gly  Val  Thr  Ser  Ala  Pro  Asp  Xaa  Arg  Pro  Xaa  Pro
          755                 760                      765

Gly  Ser  Thr  Ala  Pro  Xaa  Ala  His  Gly  Val  Thr  Ser  Ala  Pro  Asp  Xaa
     770                 775                      780

Arg  Pro  Xaa  Pro  Gly  Ser  Thr  Ala  Pro  Xaa  Ala  His  Gly  Val  Thr  Ser
785            790                      795                           800

Ala  Pro  Asp  Xaa  Arg  Pro  Xaa  Pro  Gly  Ser  Thr  Ala  Pro  Xaa  Ala  His
               805                      810                           815

Gly  Val  Thr  Ser  Ala  Pro  Asp  Xaa  Arg  Pro  Xaa  Pro  Gly  Ser  Thr  Ala
               820                 825                      830

Pro  Xaa  Ala  His  Gly  Val  Thr  Ser  Ala  Pro  Asp  Xaa  Arg  Pro  Xaa  Pro
          835                 840                      845

Gly  Ser  Thr  Ala  Pro  Xaa  Ala  His  Gly  Val  Thr  Ser  Ala  Pro  Asp  Xaa
     850                 855                      860

Arg  Pro  Xaa  Pro  Gly  Ser  Thr  Ala  Pro  Xaa  Ala  His  Gly  Val  Thr  Ser
865            870                      875                           880
```

-continued

```
Ala Pro Asp Xaa Arg Pro Xaa Pro Gly Ser Thr Ala Pro Xaa Ala His
            885             890                     895
Gly Val Thr Ser Ala Pro Asp Xaa Arg Pro Xaa Pro Gly Ser Thr Ala
        900             905                     910
Pro Xaa Ala His Gly Val Thr Ser Ala Pro Asp Xaa Arg Pro Xaa Pro
        915             920                     925
Gly Ser Thr Ala Pro Xaa Ala His Gly Val Thr Ser Ala Pro Asp Xaa
        930             935                     940
Arg Pro Xaa Pro Gly Ser Thr Ala Pro Xaa Ala His Gly Val Thr Ser
945             950             955                     960
Ala Pro Asp Xaa Arg Pro Xaa Pro Gly Ser Thr Ala Pro Xaa Ala His
            965             970                     975
Gly Val Thr Ser Ala Pro Asp Xaa Arg Pro Xaa Pro Gly Ser Thr Ala
        980             985                     990
Pro Xaa Ala His Gly Val Thr Ser Ala Pro Asp Xaa Arg Pro Xaa Pro
        995             1000                    1005
Gly Ser Thr Ala Pro Xaa Ala His Gly Val Thr Ser Ala Pro Asp Xaa
        1010            1015                    1020
Arg Pro Xaa Pro Gly Ser Thr Ala Pro Xaa Ala His Gly Val Thr Ser
1025            1030            1035                    1040
Ala Pro Asp Xaa Arg Pro Xaa Pro Gly Ser Thr Ala Pro Xaa Ala His
            1045            1050                    1055
Gly Val Thr Ser Ala Pro Asp Xaa Arg Pro Xaa Pro Gly Ser Thr Ala
        1060            1065                    1070
Pro Xaa Ala His Gly Val Thr Ser Ala Pro Asp Xaa Arg Pro Xaa Pro
        1075            1080                    1085
Gly Ser Thr Ala Pro Xaa Ala His Gly Val Thr Ser Ala Pro Asp Xaa
        1090            1095                    1100
Arg Pro Xaa Pro Gly Ser Thr Ala Pro Xaa Ala His Gly Val Thr Ser
1105            1110            1115                    1120
Ala Pro Asp Xaa Arg Pro Xaa Pro Gly Ser Thr Ala Pro Xaa Ala His
            1125            1130                    1135
Gly Val Thr Ser Ala Pro Asp Xaa Arg Pro Xaa Pro Gly Ser Thr Ala
        1140            1145                    1150
Pro Xaa Ala His Gly Val Thr Ser Ala Pro Asp Xaa Arg Pro Xaa Pro
        1155            1160                    1165
Gly Ser Thr Ala Pro Xaa Ala His Gly Val Thr Ser Ala Pro Asp Xaa
        1170            1175                    1180
Arg Pro Xaa Pro Gly Ser Thr Ala Pro Xaa Ala His Gly Val Thr Ser
1185            1190            1195                    1200
Ala Pro Asp Xaa Arg Pro Xaa Pro Gly Ser Thr Ala Pro Xaa Ala His
            1205            1210                    1215
Gly Val Thr Ser Ala Pro Asp Xaa Arg Pro Xaa Pro Gly Ser Thr Ala
        1220            1225                    1230
Pro Xaa Ala His Gly Val Thr Ser Ala Pro Asp Xaa Arg Pro Xaa Pro
        1235            1240                    1245
Gly Ser Thr Ala Pro Xaa Ala His Gly Val Thr Ser Ala Pro Asp Xaa
        1250            1255                    1260
Arg Pro Xaa Pro Gly Ser Thr Ala Pro Xaa Ala His Gly Val Thr Ser
1265            1270            1275                    1280
Ala Pro Asp Xaa Arg Pro Xaa Pro Gly Ser Thr Ala Pro Xaa Ala His
            1285            1290                    1295
```

```
Gly  Val  Thr  Ser  Ala  Pro  Asp  Xaa  Arg  Pro  Xaa  Pro  Gly  Ser  Thr  Ala
               1300                1305                     1310

Pro  Xaa  Ala  His  Gly  Val  Thr  Ser  Ala  Pro  Asp  Xaa  Arg  Pro  Xaa  Pro
          1315                     1320                     1325

Gly  Ser  Thr  Ala  Pro  Xaa  Ala  His  Gly  Val  Thr  Ser  Ala  Pro  Asp  Xaa
     1330                     1335                          1340

Arg  Pro  Xaa  Pro  Gly  Ser  Thr  Ala  Pro  Xaa  Ala  His  Gly  Val  Thr  Ser
1345                     1350                     1355                     1360

Ala  Pro  Asp  Xaa  Arg  Pro  Xaa  Pro  Gly  Ser  Thr  Ala  Pro  Xaa  Ala  His
                    1365                     1370                     1375

Gly  Val  Thr  Ser  Ala  Pro  Asp  Xaa  Arg  Pro  Xaa  Pro  Gly  Ser  Thr  Ala
               1380                     1385                     1390

Pro  Xaa  Ala  His  Gly  Val  Thr  Ser  Ala  Pro  Asp  Xaa  Arg  Pro  Xaa  Pro
          1395                     1400                     1405

Gly  Ser  Thr  Ala  Pro  Xaa  Ala  His  Gly  Val  Thr  Ser  Ala  Pro  Asp  Xaa
     1410                     1415                          1420

Arg  Pro  Xaa  Pro  Gly  Ser  Thr  Ala  Pro  Xaa  Ala  His  Gly  Val  Thr  Ser
1425                     1430                     1435                     1440

Ala  Pro  Asp  Xaa  Arg  Pro  Xaa  Pro  Gly  Ser  Thr  Ala  Pro  Xaa  Ala  His
                    1445                     1450                     1455

Gly  Val  Thr  Ser  Ala  Pro  Asp  Xaa  Arg  Pro  Xaa  Pro  Gly  Ser  Thr  Ala
               1460                     1465                     1470

Pro  Xaa  Ala  His  Gly  Val  Thr  Ser  Ala  Pro  Asp  Xaa  Arg  Pro  Xaa  Pro
          1475                     1480                     1485

Gly  Ser  Thr  Ala  Pro  Xaa  Ala  His  Gly  Val  Thr  Ser  Ala  Pro  Asp  Xaa
     1490                     1495                          1500

Arg  Pro  Xaa  Pro  Gly  Ser  Thr  Ala  Pro  Xaa  Ala  His  Gly  Val  Thr  Ser
1505                     1510                     1515                     1520

Ala  Pro  Asp  Xaa  Arg  Pro  Xaa  Pro  Gly  Ser  Thr  Ala  Pro  Xaa  Ala  His
                    1525                     1530                     1535

Gly  Val  Thr  Ser  Ala  Pro  Asp  Xaa  Arg  Pro  Xaa  Pro  Gly  Ser  Thr  Ala
               1540                     1545                     1550

Pro  Xaa  Ala  His  Gly  Val  Thr  Ser  Ala  Pro  Asp  Xaa  Arg  Pro  Xaa  Pro
          1555                     1560                     1565

Gly  Ser  Thr  Ala  Pro  Xaa  Ala  His  Gly  Val  Thr  Ser  Ala  Pro  Asp  Xaa
     1570                     1575                          1580

Arg  Pro  Xaa  Pro  Gly  Ser  Thr  Ala  Pro  Xaa  Ala  His  Gly  Val  Thr  Ser
1585                     1590                     1595                     1600

Ala  Pro  Asp  Xaa  Arg  Pro  Xaa  Pro  Gly  Ser  Thr  Ala  Pro  Xaa  Ala  His
                    1605                     1610                     1615

Gly  Val  Thr  Ser  Ala  Pro  Asp  Xaa  Arg  Pro  Xaa  Pro  Gly  Ser  Thr  Ala
               1620                     1625                     1630

Pro  Xaa  Ala  His  Gly  Val  Thr  Ser  Ala  Pro  Asp  Xaa  Arg  Pro  Xaa  Pro
          1635                     1640                     1645

Gly  Ser  Thr  Ala  Pro  Xaa  Ala  His  Gly  Val  Thr  Ser  Ala  Pro  Asp  Xaa
     1650                     1655                          1660

Arg  Pro  Xaa  Pro  Gly  Ser  Thr  Ala  Pro  Xaa  Ala  His  Gly  Val  Thr  Ser
1665                     1670                     1675                     1680

Ala  Pro  Asp  Xaa  Arg  Pro  Xaa  Pro  Gly  Ser  Thr  Ala  Pro  Xaa  Ala  His
                    1685                     1690                     1695

Gly  Val  Thr  Ser  Ala  Pro  Asp  Xaa  Arg  Pro  Xaa  Pro  Gly  Ser  Thr  Ala
               1700                     1705                     1710

Pro  Xaa  Ala  His  Gly  Val  Thr  Ser  Ala  Pro  Asp  Xaa  Arg  Pro  Xaa  Leu
          1715                     1720                     1725
```

Gly Ser Thr Ala Pro Pro Val His Asn Val Thr Ser Ala Ser Gly Ser
            1730                    1735                1740

Ala Ser Gly Ser Ala Ser Thr Leu Val His Asn Gly Thr Ser Ala Arg
1745                1750                1755                    1760

Ala Thr Thr Thr Pro Ala Ser Lys Ser Thr Pro Pro Ser Ile Pro Ser
                1765                1770                1775

His His Ser Asp Thr Pro Thr Thr Leu Ala Ser His Ser Thr Lys Thr
            1780                1785                1790

Asp Ala Ser Ser Thr His His Ser Thr Val Pro Pro Leu Thr Ser Ser
            1795                1800                1805

Asn His Ser Thr Ser Pro Gln Leu Ser Thr Gly Val Ser Phe Phe Phe
    1810                1815                1820

Leu Ser Phe His Ile Ser Asn Leu Gln Phe Asn Ser Ser Leu Glu Asp
1825                1830                1835                    1840

Pro Ser Thr Asp Tyr Tyr Gln Glu Leu Gln Arg Asp Ile Ser Glu Met
                1845                1850                1855

Phe Leu Gln Asn Tyr Lys Gln Gly Gly Phe Leu Gly Leu Ser Asn Ile
            1860                1865                1870

Lys Phe Arg Pro Glu Ser Val Val Val Gln Leu Thr Leu Ala Phe Arg
        1875                1880                1885

Glu Gly Thr Ile Asn Val His Asp Val Glu Thr Gln Phe Asn Gln Tyr
        1890                1895                1900

Lys Thr Glu Ala Ala Ser Arg Tyr Asn Leu Thr Ile Ser Asp Val Ser
1905                1910                1915                    1920

Val Ser His Val Pro Phe Pro Phe Ser Ala Gln Ser Gly Ala Gly Val
                1925                1930                1935

Pro Gly Trp Gly Ile Ala Leu Leu Val Leu Val Cys Val Leu Val Ala
            1940                1945                1950

Leu Ala Ile Val Tyr Leu Ile Ala Leu Ala Val Cys Gln Cys Arg Arg
        1955                1960                1965

Lys Asn Tyr Gly Gln Leu Asp Ile Phe Pro Ala Arg Asp Thr Tyr His
    1970                1975                1980

Pro Met Ser Glu Tyr Pro Thr Tyr His Thr His Gly Arg Tyr Val Pro
1985                1990                1995                    2000

Pro Ser Ser Thr Asp Arg Ser Pro Tyr Glu Lys Val Ser Ala Gly Asn
            2005                2010                2015

Gly Gly Ser Ser Leu Ser Tyr Thr Asn Pro Ala Val Ala Ala Thr Ser
            2020                2025                2030

Ala Asn Leu
    2035

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 7..20
        ( D ) OTHER INFORMATION: /note= "Xaa at positions 7 and 20
            is X which is Pro or Ala."

( i x ) FEATURE:
        ( A ) NAME/KEY: Peptide (B) LOCATION: 12
(D) OTHER INFORMATION: /note= "Xaa at position 12 is Y which is Thr or Asn."

(x i) SEQUENCE DESCRIPTION: SEQ ID NO:3:

| Pro | Gly | Ser | Thr | Ala | Pro | Xaa | Ala | His | Gly | Val | Thr | Ser | Ala | Pro | Asp |
|---|---|---|---|---|---|---|---|---|---|---|---|---|---|---|---|
| 1 | | | | 5 | | | | | 10 | | | | | 15 | |

| Xaa | Arg | Pro | Xaa |
|---|---|---|---|
| | | | 20 |

(2) INFORMATION FOR SEQ ID NO:4:

(i) SEQUENCE CHARACTERISTICS:
(A) LENGTH: 6449 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: sig_peptide
(B) LOCATION: 58..120

(i x) FEATURE:
(A) NAME/KEY: repeat_region
(B) LOCATION: 439..5239
(D) OTHER INFORMATION: /note= "The nucleotides spanning 439-5239 constitute a repeated region wherein the repeat is 60 nucleotides and encodes 20 amino acids, 17 of which are fixed. The number of such repeats varies from 1 to 80

(i x) FEATURE:
(A) NAME/KEY: mat_peptide
(B) LOCATION: 121..5661

(i x) FEATURE:
(A) NAME/KEY: repeat_region
(B) LOCATION: 457
(D) OTHER INFORMATION: /note= "Nucleotide 457 is X1 = NNN which is the codon for Pro or Ala wherein Pro = CCT, CCC, CCA, or CCG; and Ala = GCT, GCC, GCA, or GCG."

(i x) FEATURE:
(A) NAME/KEY: repeat_region
(B) LOCATION: 487
(D) OTHER INFORMATION: /note= "Nucleotide 487 is Y = NNN which is the codon for Thr or Asn wherein Thr = ACT, ACC, ACA, or ACG; and Asn = AAT or AAC."

(i x) FEATURE:
(A) NAME/KEY: repeat_region
(B) LOCATION: 496
(D) OTHER INFORMATION: /note= "Nucleotide 496 is X2 = NNN which is the codon for Pro or Ala wherein Pro = CCT, CCC, CCA, or CCG; and Ala = GCT, GCC, GCA, or GCG."

(x i) SEQUENCE DESCRIPTION: SEQ ID NO:4:

| | | | | | |
|---|---|---|---|---|---|
| GAATTCCCTG | GCTGCTTGAA | TCTGTTCTGC | CCCCTCCCCA | CCCATTTCAC | CACCACCATG | 60 |
| ACACCGGGCA | CCCAGTCTCC | TTTCTTCCTG | CTGCTGCTCC | TCACAGTGCT | TACAGTTGTT | 120 |
| ACAGGTTCTG | GTCATGCAAG | CTCTACCCCA | GGTGGAGAAA | AGGAGACTTC | GGCTACCCAG | 180 |
| AGAAGTTCAG | TGCCCAGCTC | TACTGAGAAG | AATGCTGTGA | GTATGACCAG | CAGCGTACTC | 240 |
| TCCAGCCACA | GCCCCGGTTC | AGGCTCCTCC | ACCACTCAGG | GACAGGATGT | CACTCTGGCC | 300 |
| CCGGCCACGG | AACCAGCTTC | AGGTTCAGCT | GCCACCTGGG | GACAGGATGT | CACCTCGGTC | 360 |
| CCAGTCACCA | GGCCAGCCCT | GGGCTCCACC | ACCCCGCCAG | CCCACGATGT | CACCTCAGCC | 420 |
| CCGGACAACA | AGCCAGCCCC | GGGCTCCACC | GCCCCNNNG | CCCACGGTGT | CACCTCGGCC | 480 |
| CCGGACNNNA | GGCCGNNNCC | GGGCTCCACC | GCCCCNNNG | CCCACGGTGT | CACCTCGGCC | 540 |

```
CCGGACNNNA GGCCGNNNCC GGGCTCCACC GCCCCCNNNG CCCACGGTGT CACCTCGGCC      600
CCGGACNNNA GGCCGNNNCC GGGCTCCACC GCCCCCNNNG CCCACGGTGT CACCTCGGCC      660
CCGGACNNNA GGCCGNNNCC GGGCTCCACC GCCCCCNNNG CCCACGGTGT CACCTCGGCC      720
CCGGACNNNA GGCCGNNNCC GGGCTCCACC GCCCCCNNNG CCCACGGTGT CACCTCGGCC      780
CCGGACNNNA GGCCGNNNCC GGGCTCCACC GCCCCCNNNG CCCACGGTGT CACCTCGGCC      840
CCGGACNNNA GGCCGNNNCC GGGCTCCACC GCCCCCNNNG CCCACGGTGT CACCTCGGCC      900
CCGGACNNNA GGCCGNNNCC GGGCTCCACC GCCCCCNNNG CCCACGGTGT CACCTCGGCC      960
CCGGACNNNA GGCCGNNNCC GGGCTCCACC GCCCCCNNNG CCCACGGTGT CACCTCGGCC     1020
CCGGACNNNA GGCCGNNNCC GGGCTCCACC GCCCCCNNNG CCCACGGTGT CACCTCGGCC     1080
CCGGACNNNA GGCCGNNNCC GGGCTCCACC GCCCCCNNNG CCCACGGTGT CACCTCGGCC     1140
CCGGACNNNA GGCCGNNNCC GGGCTCCACC GCCCCCNNNG CCCACGGTGT CACCTCGGCC     1200
CCGGACNNNA GGCCGNNNCC GGGCTCCACC GCCCCCNNNG CCCACGGTGT CACCTCGGCC     1260
CCGGACNNNA GGCCGNNNCC GGGCTCCACC GCCCCCNNNG CCCACGGTGT CACCTCGGCC     1320
CCGGACNNNA GGCCGNNNCC GGGCTCCACC GCCCCCNNNG CCCACGGTGT CACCTCGGCC     1380
CCGGACNNNA GGCCGNNNCC GGGCTCCACC GCCCCCNNNG CCCACGGTGT CACCTCGGCC     1440
CCGGACNNNA GGCCGNNNCC GGGCTCCACC GCCCCCNNNG CCCACGGTGT CACCTCGGCC     1500
CCGGACNNNA GGCCGNNNCC GGGCTCCACC GCCCCCNNNG CCCACGGTGT CACCTCGGCC     1560
CCGGACNNNA GGCCGNNNCC GGGCTCCACC GCCCCCNNNG CCCACGGTGT CACCTCGGCC     1620
CCGGACNNNA GGCCGNNNCC GGGCTCCACC GCCCCCNNNG CCCACGGTGT CACCTCGGCC     1680
CCGGACNNNA GGCCGNNNCC GGGCTCCACC GCCCCCNNNG CCCACGGTGT CACCTCGGCC     1740
CCGGACNNNA GGCCGNNNCC GGGCTCCACC GCCCCCNNNG CCCACGGTGT CACCTCGGCC     1800
CCGGACNNNA GGCCGNNNCC GGGCTCCACC GCCCCCNNNG CCCACGGTGT CACCTCGGCC     1860
CCGGACNNNA GGCCGNNNCC GGGCTCCACC GCCCCCNNNG CCCACGGTGT CACCTCGGCC     1920
CCGGACNNNA GGCCGNNNCC GGGCTCCACC GCCCCCNNNG CCCACGGTGT CACCTCGGCC     1980
CCGGACNNNA GGCCGNNNCC GGGCTCCACC GCCCCCNNNG CCCACGGTGT CACCTCGGCC     2040
CCGGACNNNA GGCCGNNNCC GGGCTCCACC GCCCCCNNNG CCCACGGTGT CACCTCGGCC     2100
CCGGACNNNA GGCCGNNNCC GGGCTCCACC GCCCCCNNNG CCCACGGTGT CACCTCGGCC     2160
CCGGACNNNA GGCCGNNNCC GGGCTCCACC GCCCCCNNNG CCCACGGTGT CACCTCGGCC     2220
CCGGACNNNA GGCCGNNNCC GGGCTCCACC GCCCCCNNNG CCCACGGTGT CACCTCGGCC     2280
CCGGACNNNA GGCCGNNNCC GGGCTCCACC GCCCCCNNNG CCCACGGTGT CACCTCGGCC     2340
CCGGACNNNA GGCCGNNNCC GGGCTCCACC GCCCCCNNNG CCCACGGTGT CACCTCGGCC     2400
CCGGACNNNA GGCCGNNNCC GGGCTCCACC GCCCCCNNNG CCCACGGTGT CACCTCGGCC     2460
CCGGACNNNA GGCCGNNNCC GGGCTCCACC GCCCCCNNNG CCCACGGTGT CACCTCGGCC     2520
CCGGACNNNA GGCCGNNNCC GGGCTCCACC GCCCCCNNNG CCCACGGTGT CACCTCGGCC     2580
CCGGACNNNA GGCCGNNNCC GGGCTCCACC GCCCCCNNNG CCCACGGTGT CACCTCGGCC     2640
CCGGACNNNA GGCCGNNNCC GGGCTCCACC GCCCCCNNNG CCCACGGTGT CACCTCGGCC     2700
CCGGACNNNA GGCCGNNNCC GGGCTCCACC GCCCCCNNNG CCCACGGTGT CACCTCGGCC     2760
CCGGACNNNA GGCCGNNNCC GGGCTCCACC GCCCCCNNNG CCCACGGTGT CACCTCGGCC     2820
CCGGACNNNA GGCCGNNNCC GGGCTCCACC GCCCCCNNNG CCCACGGTGT CACCTCGGCC     2880
CCGGACNNNA GGCCGNNNCC GGGCTCCACC GCCCCCNNNG CCCACGGTGT CACCTCGGCC     2940
```

| | | | | | | |
|---|---|---|---|---|---|---|
| CCGGACNNNA | GGCCGNNNCC | GGGCTCCACC | GCCCCCNNNG | CCCACGGTGT | CACCTCGGCC | 3000 |
| CCGGACNNNA | GGCCGNNNCC | GGGCTCCACC | GCCCCCNNNG | CCCACGGTGT | CACCTCGGCC | 3060 |
| CCGGACNNNA | GGCCGNNNCC | GGGCTCCACC | GCCCCCNNNG | CCCACGGTGT | CACCTCGGCC | 3120 |
| CCGGACNNNA | GGCCGNNNCC | GGGCTCCACC | GCCCCCNNNG | CCCACGGTGT | CACCTCGGCC | 3180 |
| CCGGACNNNA | GGCCGNNNCC | GGGCTCCACC | GCCCCCNNNG | CCCACGGTGT | CACCTCGGCC | 3240 |
| CCGGACNNNA | GGCCGNNNCC | GGGCTCCACC | GCCCCCNNNG | CCCACGGTGT | CACCTCGGCC | 3300 |
| CCGGACNNNA | GGCCGNNNCC | GGGCTCCACC | GCCCCCNNNG | CCCACGGTGT | CACCTCGGCC | 3360 |
| CCGGACNNNA | GGCCGNNNCC | GGGCTCCACC | GCCCCCNNNG | CCCACGGTGT | CACCTCGGCC | 3420 |
| CCGGACNNNA | GGCCGNNNCC | GGGCTCCACC | GCCCCCNNNG | CCCACGGTGT | CACCTCGGCC | 3480 |
| CCGGACNNNA | GGCCGNNNCC | GGGCTCCACC | GCCCCCNNNG | CCCACGGTGT | CACCTCGGCC | 3540 |
| CCGGACNNNA | GGCCGNNNCC | GGGCTCCACC | GCCCCCNNNG | CCCACGGTGT | CACCTCGGCC | 3600 |
| CCGGACNNNA | GGCCGNNNCC | GGGCTCCACC | GCCCCCNNNG | CCCACGGTGT | CACCTCGGCC | 3660 |
| CCGGACNNNA | GGCCGNNNCC | GGGCTCCACC | GCCCCCNNNG | CCCACGGTGT | CACCTCGGCC | 3720 |
| CCGGACNNNA | GGCCGNNNCC | GGGCTCCACC | GCCCCCNNNG | CCCACGGTGT | CACCTCGGCC | 3780 |
| CCGGACNNNA | GGCCGNNNCC | GGGCTCCACC | GCCCCCNNNG | CCCACGGTGT | CACCTCGGCC | 3840 |
| CCGGACNNNA | GGCCGNNNCC | GGGCTCCACC | GCCCCCNNNG | CCCACGGTGT | CACCTCGGCC | 3900 |
| CCGGACNNNA | GGCCGNNNCC | GGGCTCCACC | GCCCCCNNNG | CCCACGGTGT | CACCTCGGCC | 3960 |
| CCGGACNNNA | GGCCGNNNCC | GGGCTCCACC | GCCCCCNNNG | CCCACGGTGT | CACCTCGGCC | 4020 |
| CCGGACNNNA | GGCCGNNNCC | GGGCTCCACC | GCCCCCNNNG | CCCACGGTGT | CACCTCGGCC | 4080 |
| CCGGACNNNA | GGCCGNNNCC | GGGCTCCACC | GCCCCCNNNG | CCCACGGTGT | CACCTCGGCC | 4140 |
| CCGGACNNNA | GGCCGNNNCC | GGGCTCCACC | GCCCCCNNNG | CCCACGGTGT | CACCTCGGCC | 4200 |
| CCGGACNNNA | GGCCGNNNCC | GGGCTCCACC | GCCCCCNNNG | CCCACGGTGT | CACCTCGGCC | 4260 |
| CCGGACNNNA | GGCCGNNNCC | GGGCTCCACC | GCCCCCNNNG | CCCACGGTGT | CACCTCGGCC | 4320 |
| CCGGACNNNA | GGCCGNNNCC | GGGCTCCACC | GCCCCCNNNG | CCCACGGTGT | CACCTCGGCC | 4380 |
| CCGGACNNNA | GGCCGNNNCC | GGGCTCCACC | GCCCCCNNNG | CCCACGGTGT | CACCTCGGCC | 4440 |
| CCGGACNNNA | GGCCGNNNCC | GGGCTCCACC | GCCCCCNNNG | CCCACGGTGT | CACCTCGGCC | 4500 |
| CCGGACNNNA | GGCCGNNNCC | GGGCTCCACC | GCCCCCNNNG | CCCACGGTGT | CACCTCGGCC | 4560 |
| CCGGACNNNA | GGCCGNNNCC | GGGCTCCACC | GCCCCCNNNG | CCCACGGTGT | CACCTCGGCC | 4620 |
| CCGGACNNNA | GGCCGNNNCC | GGGCTCCACC | GCCCCCNNNG | CCCACGGTGT | CACCTCGGCC | 4680 |
| CCGGACNNNA | GGCCGNNNCC | GGGCTCCACC | GCCCCCNNNG | CCCACGGTGT | CACCTCGGCC | 4740 |
| CCGGACNNNA | GGCCGNNNCC | GGGCTCCACC | GCCCCCNNNG | CCCACGGTGT | CACCTCGGCC | 4800 |
| CCGGACNNNA | GGCCGNNNCC | GGGCTCCACC | GCCCCCNNNG | CCCACGGTGT | CACCTCGGCC | 4860 |
| CCGGACNNNA | GGCCGNNNCC | GGGCTCCACC | GCCCCCNNNG | CCCACGGTGT | CACCTCGGCC | 4920 |
| CCGGACNNNA | GGCCGNNNCC | GGGCTCCACC | GCCCCCNNNG | CCCACGGTGT | CACCTCGGCC | 4980 |
| CCGGACNNNA | GGCCGNNNCC | GGGCTCCACC | GCCCCCNNNG | CCCACGGTGT | CACCTCGGCC | 5040 |
| CCGGACNNNA | GGCCGNNNCC | GGGCTCCACC | GCCCCCNNNG | CCCACGGTGT | CACCTCGGCC | 5100 |
| CCGGACNNNA | GGCCGNNNCC | GGGCTCCACC | GCCCCCNNNG | CCCACGGTGT | CACCTCGGCC | 5160 |
| CCGGACNNNA | GGCCGNNNCC | GGGCTCCACC | GCCCCCNNNG | CCCACGGTGT | CACCTCGGCC | 5220 |
| CCGGACNNNA | GGCCGNNNTT | GGGCTCCACC | GCCCCTCCAG | TCCACAATGT | CACCTCGGCC | 5280 |
| TCAGGCTCTG | CATCAGGCTC | AGCTTCTACT | CTGGTGCACA | ACGGCACCTC | TGCCAGGGCT | 5340 |

-continued

| | | | | | | |
|---|---|---|---|---|---|---|
| ACCACAACCC | CAGCCAGCAA | GAGCACTCCA | TTCTCAATTC | CCAGCCACCA | CTCTGATACT | 5400 |
| CCTACCACCC | TTGCCAGCCA | TAGCACCAAG | ACTGATGCCA | GTAGCACTCA | CCATAGCACG | 5460 |
| GTACCTCCTC | TCACCTCCTC | CAATCACAGC | ACTTCTCCCC | AGTTGTCTAC | TGGGGTCTCT | 5520 |
| TTCTTTTTCC | TGTCTTTTCA | CATTTCAAAC | CTCCAGTTTA | ATTCCTCTCT | GGAAGATCCC | 5580 |
| AGCACCGACT | ACTACCAAGA | GCTGCAGAGA | GACATTTCTG | AAATGGTGAG | TATCGGCTTT | 5640 |
| TCCTTCCCCA | TGCTCCCCTG | AAGCAGCCAT | CAGAACTGTC | CACACCCTTT | GCATCAAGCC | 5700 |
| TGAGTCCTTT | CCCTCTCACC | CCAGTTTTG | CAGATTTATA | AACAAGGGGG | TTTTCTGGGC | 5760 |
| CTCTCCAATA | TTAAGTTCAG | GTACAGTTCT | GGGTGTGGAC | CCAGTGTGGT | GGTTGGAGGG | 5820 |
| TTGGGTGGTG | GTCATGACCG | TAGGAGGGAC | TGGTCGCACT | TAAGGTTGGG | GGAAGAGTCG | 5880 |
| TGAGCCAGAG | CTGGGACCCG | TGGCTGAAGT | GCCCATTTCC | CTGTGACCAG | GCCAGGATCT | 5940 |
| GTGGTGGTAC | AATTGACTCT | GGCCTTCCGA | GAAGGTACCA | TCAATGTCCA | CGACGTGGAG | 6000 |
| ACACAGTTCA | ATCAGTATAA | AACGGAAGCA | GCCTCTCGAT | ATAACCTGAC | GATCTCAGAC | 6060 |
| GTCAGCGGTG | AGGCTACTTC | CCTGGCTGCA | GCCCAGCACC | ATGCCGGGGC | CCTCTCCTTC | 6120 |
| CAGTGCCTGG | GTCCCCGCTC | TTTCCTTAGT | GCTGGCAGCG | GGAGGGGCGC | CTCCTCTGGG | 6180 |
| AGACTGCCCT | GACCACTGCT | TTTCCTTTTA | GTGAGTCATG | TGCCATTTCC | TTTCTCTGCC | 6240 |
| CAGTCTGGGG | CTGGGGTGCC | AGGCTGGGGC | ATCGCGCTGC | TGGTGCTGGT | CTGTGTTCTG | 6300 |
| GTTGCGCTGG | CCATTGTCTA | TCTCATTGCC | TTGGTGAGTG | CAGTCCCTGG | CCCTGATCAG | 6360 |
| AGCCCCCCGT | TAGAAGGCAC | TCCATGGCCT | GCCATAACCT | CCTATCTCCC | CAGGCTGTCT | 6420 |
| GTCAGTGCCG | CCGAAAGAAC | TACGGGCAG | | | | 6449 |

(2) INFORMATION FOR SEQ ID NO:5:

(i) SEQUENCE CHARACTERISTICS:
        (A) LENGTH: 1867 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 128..1727
        (D) OTHER INFORMATION: /note= "The amino acids spanning
            128 to 1727 constitute a repeated region wherein the
            repeat is 20 amino acids, 17 of which are fixed. The
            number of such repeats varies from 1 to 40."

(ix) FEATURE:
        (A) NAME/KEY: Peptide
        (B) LOCATION: 134
        (D) OTHER INFORMATION: /note= "Amino acid 134 is X1 = Xaa
            which is the codon for Pro or Ala wherein Pro = CCT, CCC,
            CCA, or CCG; and Ala = GCT, GCC, GCA, or GCG."

(ix) FEATURE:
        (A) NAME/KEY: Peptide
        (B) LOCATION: 144
        (D) OTHER INFORMATION: /note= "Amino acid 144 is Y = Xaa
            which is the codon for Thr or Asn wherein Thr = ACT, ACC,
            ACA, or ACG; and Asn = AAT or AAC."

(ix) FEATURE:
        (A) NAME/KEY: Peptide
        (B) LOCATION: 147
        (D) OTHER INFORMATION: /note= "Amino acid 147 is X2 = Xaa
            which is the codon for Pro or Ala wherein Pro = CCT, CCC,
            CCA, or CCG; and Ala = GCT, GCC, GCA, or GCG."

(ix) FEATURE:
        (A) NAME/KEY: Peptide (B) LOCATION: 1..21
(D) OTHER INFORMATION: /note= "Amino acids 1 to 21 are a 21 amino acid precursor sequence."

(xi) SEQUENCE DESCRIPTION: SEQ ID NO:5:

| Met | Thr | Pro | Gly | Thr | Gln | Ser | Pro | Phe | Phe | Leu | Leu | Leu | Leu | Thr |
|---|---|---|---|---|---|---|---|---|---|---|---|---|---|---|
| 1 | | | | 5 | | | | | 10 | | | | | 15 |
| Val | Leu | Thr | Val | Val | Thr | Gly | Ser | Gly | His | Ala | Ser | Ser | Thr | Pro | Gly |
| | | | 20 | | | | | 25 | | | | | 30 | | |
| Gly | Glu | Lys | Glu | Thr | Ser | Ala | Thr | Gln | Arg | Ser | Ser | Val | Pro | Ser | Ser |
| | | 35 | | | | | 40 | | | | | 45 | | | |
| Thr | Glu | Lys | Asn | Ala | Val | Ser | Met | Thr | Ser | Ser | Val | Leu | Ser | Ser | His |
| | 50 | | | | | 55 | | | | | 60 | | | | |
| Ser | Pro | Gly | Ser | Gly | Ser | Ser | Thr | Thr | Gln | Gly | Gln | Asp | Val | Thr | Leu |
| 65 | | | | | 70 | | | | | 75 | | | | | 80 |
| Ala | Pro | Ala | Thr | Glu | Pro | Ala | Ser | Gly | Ser | Ala | Ala | Thr | Trp | Gly | Gln |
| | | | | 85 | | | | | 90 | | | | | 95 | |
| Asp | Val | Thr | Ser | Val | Pro | Val | Thr | Arg | Pro | Ala | Leu | Gly | Ser | Thr | Thr |
| | | | 100 | | | | | 105 | | | | | 110 | | |
| Pro | Pro | Ala | His | Asp | Val | Thr | Ser | Ala | Pro | Asp | Asn | Lys | Pro | Ala | Pro |
| | | | 115 | | | | | 120 | | | | | 125 | | |
| Gly | Ser | Thr | Ala | Pro | Xaa | Ala | His | Gly | Val | Thr | Ser | Ala | Pro | Asp | Xaa |
| | | 130 | | | | | 135 | | | | | 140 | | | |
| Arg | Pro | Xaa | Pro | Gly | Ser | Thr | Ala | Pro | Xaa | Ala | His | Gly | Val | Thr | Ser |
| 145 | | | | | 150 | | | | | 155 | | | | | 160 |
| Ala | Pro | Asp | Xaa | Arg | Pro | Xaa | Pro | Gly | Ser | Thr | Ala | Pro | Xaa | Ala | His |
| | | | | 165 | | | | | 170 | | | | | 175 | |
| Gly | Val | Thr | Ser | Ala | Pro | Asp | Xaa | Arg | Pro | Xaa | Pro | Gly | Ser | Thr | Ala |
| | | | 180 | | | | | 185 | | | | | 190 | | |
| Pro | Xaa | Ala | His | Gly | Val | Thr | Ser | Ala | Pro | Asp | Xaa | Arg | Pro | Xaa | Pro |
| | | 195 | | | | | 200 | | | | | 205 | | | |
| Gly | Ser | Thr | Ala | Pro | Xaa | Ala | His | Gly | Val | Thr | Ser | Ala | Pro | Asp | Xaa |
| | | 210 | | | | | 215 | | | | | 220 | | | |
| Arg | Pro | Xaa | Pro | Gly | Ser | Thr | Ala | Pro | Xaa | Ala | His | Gly | Val | Thr | Ser |
| 225 | | | | | 230 | | | | | 235 | | | | | 240 |
| Ala | Pro | Asp | Xaa | Arg | Pro | Xaa | Pro | Gly | Ser | Thr | Ala | Pro | Xaa | Ala | His |
| | | | | 245 | | | | | 250 | | | | | 255 | |
| Gly | Val | Thr | Ser | Ala | Pro | Asp | Xaa | Arg | Pro | Xaa | Pro | Gly | Ser | Thr | Ala |
| | | | 260 | | | | | 265 | | | | | 270 | | |
| Pro | Xaa | Ala | His | Gly | Val | Thr | Ser | Ala | Pro | Asp | Xaa | Arg | Pro | Xaa | Pro |
| | | 275 | | | | | 280 | | | | | 285 | | | |
| Gly | Ser | Thr | Ala | Pro | Xaa | Ala | His | Gly | Val | Thr | Ser | Ala | Pro | Asp | Xaa |
| | | 290 | | | | | 295 | | | | | 300 | | | |
| Arg | Pro | Xaa | Pro | Gly | Ser | Thr | Ala | Pro | Xaa | Ala | His | Gly | Val | Thr | Ser |
| 305 | | | | | 310 | | | | | 315 | | | | | 320 |
| Ala | Pro | Asp | Xaa | Arg | Pro | Xaa | Pro | Gly | Ser | Thr | Ala | Pro | Xaa | Ala | His |
| | | | | 325 | | | | | 330 | | | | | 335 | |
| Gly | Val | Thr | Ser | Ala | Pro | Asp | Xaa | Arg | Pro | Xaa | Pro | Gly | Ser | Thr | Ala |
| | | | 340 | | | | | 345 | | | | | 350 | | |
| Pro | Xaa | Ala | His | Gly | Val | Thr | Ser | Ala | Pro | Asp | Xaa | Arg | Pro | Xaa | Pro |
| | | 355 | | | | | 360 | | | | | 365 | | | |
| Gly | Ser | Thr | Ala | Pro | Xaa | Ala | His | Gly | Val | Thr | Ser | Ala | Pro | Asp | Xaa |
| | | 370 | | | | | 375 | | | | | 380 | | | |
| Arg | Pro | Xaa | Pro | Gly | Ser | Thr | Ala | Pro | Xaa | Ala | His | Gly | Val | Thr | Ser |
| 385 | | | | | 390 | | | | | 395 | | | | | 400 |

-continued

```
Ala  Pro  Asp  Xaa  Arg  Pro  Xaa  Pro  Gly  Ser  Thr  Ala  Pro  Xaa  Ala  His
               405                410                     415

Gly  Val  Thr  Ser  Ala  Pro  Asp  Xaa  Arg  Pro  Xaa  Pro  Gly  Ser  Thr  Ala
               420                425                     430

Pro  Xaa  Ala  His  Gly  Val  Thr  Ser  Ala  Pro  Asp  Xaa  Arg  Pro  Xaa  Pro
          435                440                     445

Gly  Ser  Thr  Ala  Pro  Xaa  Ala  His  Gly  Val  Thr  Ser  Ala  Pro  Asp  Xaa
     450                455                     460

Arg  Pro  Xaa  Pro  Gly  Ser  Thr  Ala  Pro  Xaa  Ala  His  Gly  Val  Thr  Ser
465                     470                     475                          480

Ala  Pro  Asp  Xaa  Arg  Pro  Xaa  Pro  Gly  Ser  Thr  Ala  Pro  Xaa  Ala  His
               485                490                     495

Gly  Val  Thr  Ser  Ala  Pro  Asp  Xaa  Arg  Pro  Xaa  Pro  Gly  Ser  Thr  Ala
               500                505                     510

Pro  Xaa  Ala  His  Gly  Val  Thr  Ser  Ala  Pro  Asp  Xaa  Arg  Pro  Xaa  Pro
          515                520                     525

Gly  Ser  Thr  Ala  Pro  Xaa  Ala  His  Gly  Val  Thr  Ser  Ala  Pro  Asp  Xaa
     530                535                     540

Arg  Pro  Xaa  Pro  Gly  Ser  Thr  Ala  Pro  Xaa  Ala  His  Gly  Val  Thr  Ser
545                     550                     555                          560

Ala  Pro  Asp  Xaa  Arg  Pro  Xaa  Pro  Gly  Ser  Thr  Ala  Pro  Xaa  Ala  His
               565                570                     575

Gly  Val  Thr  Ser  Ala  Pro  Asp  Xaa  Arg  Pro  Xaa  Pro  Gly  Ser  Thr  Ala
               580                585                     590

Pro  Xaa  Ala  His  Gly  Val  Thr  Ser  Ala  Pro  Asp  Xaa  Arg  Pro  Xaa  Pro
          595                600                     605

Gly  Ser  Thr  Ala  Pro  Xaa  Ala  His  Gly  Val  Thr  Ser  Ala  Pro  Asp  Xaa
     610                615                     620

Arg  Pro  Xaa  Pro  Gly  Ser  Thr  Ala  Pro  Xaa  Ala  His  Gly  Val  Thr  Ser
625                     630                     635                          640

Ala  Pro  Asp  Xaa  Arg  Pro  Xaa  Pro  Gly  Ser  Thr  Ala  Pro  Xaa  Ala  His
               645                650                     655

Gly  Val  Thr  Ser  Ala  Pro  Asp  Xaa  Arg  Pro  Xaa  Pro  Gly  Ser  Thr  Ala
               660                665                     670

Pro  Xaa  Ala  His  Gly  Val  Thr  Ser  Ala  Pro  Asp  Xaa  Arg  Pro  Xaa  Pro
          675                680                     685

Gly  Ser  Thr  Ala  Pro  Xaa  Ala  His  Gly  Val  Thr  Ser  Ala  Pro  Asp  Xaa
     690                695                     700

Arg  Pro  Xaa  Pro  Gly  Ser  Thr  Ala  Pro  Xaa  Ala  His  Gly  Val  Thr  Ser
705                     710                     715                          720

Ala  Pro  Asp  Xaa  Arg  Pro  Xaa  Pro  Gly  Ser  Thr  Ala  Pro  Xaa  Ala  His
               725                730                     735

Gly  Val  Thr  Ser  Ala  Pro  Asp  Xaa  Arg  Pro  Xaa  Pro  Gly  Ser  Thr  Ala
               740                745                     750

Pro  Xaa  Ala  His  Gly  Val  Thr  Ser  Ala  Pro  Asp  Xaa  Arg  Pro  Xaa  Pro
          755                760                     765

Gly  Ser  Thr  Ala  Pro  Xaa  Ala  His  Gly  Val  Thr  Ser  Ala  Pro  Asp  Xaa
     770                775                     780

Arg  Pro  Xaa  Pro  Gly  Ser  Thr  Ala  Pro  Xaa  Ala  His  Gly  Val  Thr  Ser
785                     790                     795                          800

Ala  Pro  Asp  Xaa  Arg  Pro  Xaa  Pro  Gly  Ser  Thr  Ala  Pro  Xaa  Ala  His
               805                810                     815
```

-continued

```
Gly  Val  Thr  Ser  Ala  Pro  Asp  Xaa  Arg  Pro  Xaa  Pro  Gly  Ser  Thr  Ala
               820                 825                           830

Pro  Xaa  Ala  His  Gly  Val  Thr  Ser  Ala  Pro  Asp  Xaa  Arg  Pro  Xaa  Pro
          835                      840                      845

Gly  Ser  Thr  Ala  Pro  Xaa  Ala  His  Gly  Val  Thr  Ser  Ala  Pro  Asp  Xaa
850                           855                           860

Arg  Pro  Xaa  Pro  Gly  Ser  Thr  Ala  Pro  Xaa  Ala  His  Gly  Val  Thr  Ser
865                      870                      875                      880

Ala  Pro  Asp  Xaa  Arg  Pro  Xaa  Pro  Gly  Ser  Thr  Ala  Pro  Xaa  Ala  His
                    885                      890                           895

Gly  Val  Thr  Ser  Ala  Pro  Asp  Xaa  Arg  Pro  Xaa  Pro  Gly  Ser  Thr  Ala
               900                 905                           910

Pro  Xaa  Ala  His  Gly  Val  Thr  Ser  Ala  Pro  Asp  Xaa  Arg  Pro  Xaa  Pro
          915                      920                      925

Gly  Ser  Thr  Ala  Pro  Xaa  Ala  His  Gly  Val  Thr  Ser  Ala  Pro  Asp  Xaa
930                           935                           940

Arg  Pro  Xaa  Pro  Gly  Ser  Thr  Ala  Pro  Xaa  Ala  His  Gly  Val  Thr  Ser
945                      950                      955                      960

Ala  Pro  Asp  Xaa  Arg  Pro  Xaa  Pro  Gly  Ser  Thr  Ala  Pro  Xaa  Ala  His
                    965                      970                           975

Gly  Val  Thr  Ser  Ala  Pro  Asp  Xaa  Arg  Pro  Xaa  Pro  Gly  Ser  Thr  Ala
               980                 985                           990

Pro  Xaa  Ala  His  Gly  Val  Thr  Ser  Ala  Pro  Asp  Xaa  Arg  Pro  Xaa  Pro
          995                      1000                     1005

Gly  Ser  Thr  Ala  Pro  Xaa  Ala  His  Gly  Val  Thr  Ser  Ala  Pro  Asp  Xaa
1010                          1015                          1020

Arg  Pro  Xaa  Pro  Gly  Ser  Thr  Ala  Pro  Xaa  Ala  His  Gly  Val  Thr  Ser
1025                     1030                     1035                     1040

Ala  Pro  Asp  Xaa  Arg  Pro  Xaa  Pro  Gly  Ser  Thr  Ala  Pro  Xaa  Ala  His
                    1045                     1050                          1055

Gly  Val  Thr  Ser  Ala  Pro  Asp  Xaa  Arg  Pro  Xaa  Pro  Gly  Ser  Thr  Ala
               1060                1065                          1070

Pro  Xaa  Ala  His  Gly  Val  Thr  Ser  Ala  Pro  Asp  Xaa  Arg  Pro  Xaa  Pro
          1075                     1080                     1085

Gly  Ser  Thr  Ala  Pro  Xaa  Ala  His  Gly  Val  Thr  Ser  Ala  Pro  Asp  Xaa
1090                          1095                          1100

Arg  Pro  Xaa  Pro  Gly  Ser  Thr  Ala  Pro  Xaa  Ala  His  Gly  Val  Thr  Ser
1105                     1110                     1115                     1120

Ala  Pro  Asp  Xaa  Arg  Pro  Xaa  Pro  Gly  Ser  Thr  Ala  Pro  Xaa  Ala  His
                    1125                     1130                          1135

Gly  Val  Thr  Ser  Ala  Pro  Asp  Xaa  Arg  Pro  Xaa  Pro  Gly  Ser  Thr  Ala
               1140                1145                          1150

Pro  Xaa  Ala  His  Gly  Val  Thr  Ser  Ala  Pro  Asp  Xaa  Arg  Pro  Xaa  Pro
          1155                     1160                     1165

Gly  Ser  Thr  Ala  Pro  Xaa  Ala  His  Gly  Val  Thr  Ser  Ala  Pro  Asp  Xaa
1170                          1175                          1180

Arg  Pro  Xaa  Pro  Gly  Ser  Thr  Ala  Pro  Xaa  Ala  His  Gly  Val  Thr  Ser
1185                     1190                     1195                     1200

Ala  Pro  Asp  Xaa  Arg  Pro  Xaa  Pro  Gly  Ser  Thr  Ala  Pro  Xaa  Ala  His
                    1205                     1210                          1215

Gly  Val  Thr  Ser  Ala  Pro  Asp  Xaa  Arg  Pro  Xaa  Pro  Gly  Ser  Thr  Ala
               1220                1225                          1230

Pro  Xaa  Ala  His  Gly  Val  Thr  Ser  Ala  Pro  Asp  Xaa  Arg  Pro  Xaa  Pro
          1235                     1240                     1245
```

```
Gly Ser Thr Ala Pro Xaa Ala His Gly Val Thr Ser Ala Pro Asp Xaa
    1250                1255                    1260

Arg Pro Xaa Pro Gly Ser Thr Ala Pro Xaa Ala His Gly Val Thr Ser
1265                1270                    1275                1280

Ala Pro Asp Xaa Arg Pro Xaa Pro Gly Ser Thr Ala Pro Xaa Ala His
                1285                    1290                    1295

Gly Val Thr Ser Ala Pro Asp Xaa Arg Pro Xaa Pro Gly Ser Thr Ala
            1300                    1305                    1310

Pro Xaa Ala His Gly Val Thr Ser Ala Pro Asp Xaa Arg Pro Xaa Pro
        1315                    1320                    1325

Gly Ser Thr Ala Pro Xaa Ala His Gly Val Thr Ser Ala Pro Asp Xaa
    1330                1335                    1340

Arg Pro Xaa Pro Gly Ser Thr Ala Pro Xaa Ala His Gly Val Thr Ser
1345                1350                    1355                1360

Ala Pro Asp Xaa Arg Pro Xaa Pro Gly Ser Thr Ala Pro Xaa Ala His
                1365                    1370                    1375

Gly Val Thr Ser Ala Pro Asp Xaa Arg Pro Xaa Pro Gly Ser Thr Ala
            1380                    1385                    1390

Pro Xaa Ala His Gly Val Thr Ser Ala Pro Asp Xaa Arg Pro Xaa Pro
        1395                    1400                    1405

Gly Ser Thr Ala Pro Xaa Ala His Gly Val Thr Ser Ala Pro Asp Xaa
    1410                1415                    1420

Arg Pro Xaa Pro Gly Ser Thr Ala Pro Xaa Ala His Gly Val Thr Ser
1425                1430                    1435                1440

Ala Pro Asp Xaa Arg Pro Xaa Pro Gly Ser Thr Ala Pro Xaa Ala His
                1445                    1450                    1455

Gly Val Thr Ser Ala Pro Asp Xaa Arg Pro Xaa Pro Gly Ser Thr Ala
            1460                    1465                    1470

Pro Xaa Ala His Gly Val Thr Ser Ala Pro Asp Xaa Arg Pro Xaa Pro
        1475                    1480                    1485

Gly Ser Thr Ala Pro Xaa Ala His Gly Val Thr Ser Ala Pro Asp Xaa
    1490                1495                    1500

Arg Pro Xaa Pro Gly Ser Thr Ala Pro Xaa Ala His Gly Val Thr Ser
1505                1510                    1515                1520

Ala Pro Asp Xaa Arg Pro Xaa Pro Gly Ser Thr Ala Pro Xaa Ala His
                1525                    1530                    1535

Gly Val Thr Ser Ala Pro Asp Xaa Arg Pro Xaa Pro Gly Ser Thr Ala
            1540                    1545                    1550

Pro Xaa Ala His Gly Val Thr Ser Ala Pro Asp Xaa Arg Pro Xaa Pro
        1555                    1560                    1565

Gly Ser Thr Ala Pro Xaa Ala His Gly Val Thr Ser Ala Pro Asp Xaa
    1570                1575                    1580

Arg Pro Xaa Pro Gly Ser Thr Ala Pro Xaa Ala His Gly Val Thr Ser
1585                1590                    1595                1600

Ala Pro Asp Xaa Arg Pro Xaa Pro Gly Ser Thr Ala Pro Xaa Ala His
                1605                    1610                    1615

Gly Val Thr Ser Ala Pro Asp Xaa Arg Pro Xaa Pro Gly Ser Thr Ala
            1620                    1625                    1630

Pro Xaa Ala His Gly Val Thr Ser Ala Pro Asp Xaa Arg Pro Xaa Pro
        1635                    1640                    1645

Gly Ser Thr Ala Pro Xaa Ala His Gly Val Thr Ser Ala Pro Asp Xaa
    1650                1655                    1660
```

-continued

```
Arg Pro Xaa Pro Gly Ser Thr Ala Pro Xaa Ala His Gly Val Thr Ser
1665            1670            1675                1680

Ala Pro Asp Xaa Arg Pro Xaa Pro Gly Ser Thr Ala Pro Xaa Ala His
            1685            1690            1695

Gly Val Thr Ser Ala Pro Asp Xaa Arg Pro Xaa Pro Gly Ser Thr Ala
            1700            1705            1710

Pro Xaa Ala His Gly Val Thr Ser Ala Pro Asp Xaa Arg Pro Xaa Leu
        1715            1720            1725

Gly Ser Thr Ala Pro Pro Val His Asn Val Thr Ser Ala Ser Gly Ser
    1730            1735            1740

Ala Ser Gly Ser Ala Ser Thr Leu Val His Asn Gly Thr Ser Ala Arg
1745            1750            1755            1760

Ala Thr Thr Thr Pro Ala Ser Lys Ser Thr Pro Phe Ser Ile Pro Ser
            1765            1770            1775

His His Ser Asp Thr Pro Thr Thr Leu Ala Ser His Ser Thr Lys Thr
            1780            1785            1790

Asp Ala Ser Ser Thr His His Ser Thr Val Pro Pro Leu Thr Ser Ser
        1795            1800            1805

Asn His Ser Thr Ser Pro Gln Leu Ser Thr Gly Val Ser Phe Phe Phe
    1810            1815            1820

Leu Ser Phe His Ile Ser Asn Leu Gln Phe Asn Ser Ser Leu Glu Asp
1825            1830            1835            1840

Pro Ser Thr Asp Tyr Tyr Gln Glu Leu Gln Arg Asp Ile Ser Glu Met
            1845            1850            1855

Val Ser Ile Gly Leu Ser Phe Pro Met Leu Pro
        1860            1865
```

We claim:

1. A pharmaceutical composition which comprises, as therapeutic agent, a vaccinia virus into the genome of which a DNA fragment coding for a polypeptide recognized by antibody H23 is inserted, said DNA fragment being placed under the control of suitable transcription and translation signals; said polypeptide comprising a sequence repeated n times, n being a number from 1 to 80; and of formula (I): Pro-Gly-Ser-Thr-Ala-Pro-$X_1$-Ala-His-Gly-Val-Thr-Ser-Ala-Pro-Asp-Y-Arg-Pro-$X_2$ (SEQ. ID. NO. 3) in which $X_1$ and $X_2$ are, independently, Pro or Ala and Y is Thr or Asn; and said polypeptide comprising a sequence selected from the group consisting of (i) the sequence as shown in SEQ. ID No. 2 beginning with the threonine residue at position 22 and ending with the leucine residue at position 2035 or a sequence identical thereto except that the number of repeated sequences having SEQ. ID. No. 3 ranges from 1 to 79, (ii) the sequence as shown in SEQ. ID. No. 5 beginning with the threonine residue at position 22 and ending with the proline residue at position 1867, or a sequence identical thereto, except that the number of repeated sequences having SEQ ID NO. 3 ranges from 1 to 79, (iii) variants of the sequences set forth in (i) or (ii), wherein such variants differ from the sequence set forth in (i) or (ii), only in the fact that one or more of the repeat sequences contained therein differs from the repeat sequence of SEQ. ID. NO. 3 at no more than three amino acid positions, and (iv) fragments of any of said sequences set forth in (i), (ii) or (iii), wherein said fragment is a polypeptide that is recognized by antibody H23.

2. A composition according to claim 1, which comprises a vaccinia virus into the genome of which a DNA fragment coding for a polypeptide recognized by antibody H23 is inserted, said polypeptide having as its sequence (i) the sequence as shown in SEQ. ID. No. 2 beginning with the threonine residue at position 22 and ending with the leucine residue at position 2035, except that the number of repeated sequences having SEQ. ID. No. 3 ranges from 2 to 4, or (ii) the sequence as shown in SEQ. ID. No. 5, beginning with the threonine residue at position 22 and ending with the proline residue at position 1867, except that the number of repeated sequences having SEQ. ID. No. 3 ranges from 2 to 4.

3. The pharmaceutical composition of claim 1, wherein $X_1$ is Pro.

4. The pharmaceutical composition of claim 1, wherein $X_1$ is Ala.

5. The pharmaceutical composition of claim 1, wherein $X_2$ is Pro.

6. The pharmaceutical composition of claim 1, wherein $X_2$ is Ala.

7. The pharmaceutical composition of claim 1, wherein Y is Thr.

8. The pharmaceutical composition of claim 1, wherein Y is Asn.

9. The pharmaceutical composition of claim 1, wherein the polypeptide has the sequence shown in SEQ ID. No. 5, and the number of repeats n of SEQ. ID. No. 3 is 2, 3 or 4.

10. The pharmaceutical composition according to claim 1, wherein the number of repeated sequences in the polypeptide ranges from 1 to 40.

11. The pharmaceutical composition of claim 1, wherein the polypeptide has the sequence shown in SEQ. ID. No. 2, and the number of repeats n of SEQ. ID. No.3 is 2, 3 or 4.

12. The pharmaceutical composition of claim 9, wherein n is 4.

13. The pharmaceutical composition of claim 11, wherein n is 4.

* * * * *

UNITED STATES PATENT AND TRADEMARK OFFICE
CERTIFICATE OF CORRECTION

PATENT NO. : 5,861,381
DATED : January 19, 1999
INVENTOR(S) : Pierre Chambon et al.

It is certified that error appears in the above-indentified patent and that said Letters Patent is hereby corrected as shown below:

On the title page, item: [30], please insert
--Oct. 23, 1991 [PCT]  PCT/FR91/00835--.

Signed and Sealed this

Twenty-ninth Day of August, 2000

Attest:

Q. TODD DICKINSON

Attesting Officer

Director of Patents and Trademarks